(12) United States Patent
Das et al.

(10) Patent No.: US 8,252,561 B2
(45) Date of Patent: Aug. 28, 2012

(54) PRODUCTION OF BIOFUEL USING MOLLUSCAN PSEUDOFECES DERIVED FROM ALGAL CELLS

(75) Inventors: Keshav C. Das, Athens, GA (US); Senthil Chinnasamy, Tamilnadu (IN); James Shelton, Athens, GA (US); Susan B. Wilde, Watkinsville, GA (US); Rebecca S. Haynie, Carlton, GA (US); James A. Herrin, Atlanta, GA (US)

(73) Assignee: University of Georgia Research Foundation, Inc., Athens, GA (US)

( * ) Notice: Subject to any disclaimer, the term of this patent is extended or adjusted under 35 U.S.C. 154(b) by 234 days.

(21) Appl. No.: 12/862,246

(22) Filed: Aug. 24, 2010

(65) Prior Publication Data

US 2011/0045556 A1  Feb. 24, 2011

Related U.S. Application Data

(60) Provisional application No. 61/236,323, filed on Aug. 24, 2009.

(51) Int. Cl.
*C12P 7/64* (2006.01)
*C12N 1/12* (2006.01)
*A01K 61/00* (2006.01)
*C11B 1/00* (2006.01)

(52) U.S. Cl. ............... 435/134; 435/257.1; 119/234; 554/8; 554/20; 554/23

(58) Field of Classification Search .............. 119/234; 435/134, 257.1; 554/8, 20, 23
See application file for complete search history.

(56) References Cited

U.S. PATENT DOCUMENTS

2010/0077654 A1* 4/2010 Wu et al. ............ 44/385

FOREIGN PATENT DOCUMENTS

JP   2005081330 A   * 3/2005

OTHER PUBLICATIONS

Derwent Abstract for JP2005081330.*
Machine translation of JP2005081330 provided by JPO website.*

* cited by examiner

*Primary Examiner* — Blaine Lankford
*Assistant Examiner* — Charles Zoltan Constantine
(74) *Attorney, Agent, or Firm* — Thomas, Kayden, Horstemeyer & Risley, LLP

(57) ABSTRACT

Embodiments of the present disclosure provide for novel strategies to harvest algal lipids using mollusks which after feeding algae from the growth medium can convert algal lipids into their biomass or excrete lipids in their pseudofeces which makes algae harvesting energy efficient and cost effective. The bioconverter, filter-feeding mollusks and their pseudofeces can be harvested and converted to biocrude using an advanced thermochemical liquefaction technology. Methods, systems, and materials are disclosed for the harvest and isolation of algal lipids from the mollusks, molluscan feces and molluscan pseudofeces.

15 Claims, 14 Drawing Sheets

PRODUCTION OF BIOFUEL USING MOLLUSCAN PSEUDOFECES DERIVED FROM ALGAL CELLS

CROSS-REFERENCE TO RELATED APPLICATIONS

This application claims priority to U.S. Provisional Patent Application Ser. No. 61/236,323, entitled "ALGAL LIPID HARVEST FROM MOLLUSKS FOR BIOFUELS PRODUCTION" filed on Aug. 24, 2009, the entirety of which is hereby incorporated by reference.

STATEMENT OF GOVERNMENTAL SUPPORT

This invention was made with government support under grant number DE-FG36-08GO88114 awarded by the Department of Energy (DOE) of the United States government. The government has certain rights in the invention.

TECHNICAL FIELD

The present disclosure is generally related to the methods of harvesting microalgae and algal-derived lipids using mollusk beds. The present disclosure is further generally related to the systems and methods of obtaining biofuel from the tissues of mollusk beds cultured on microalgae.

BACKGROUND

Microalgae offer great promise to contribute a significant portion of the renewable fuels that will be required to meet the U.S. biofuel production target of 36 billion gallons by 2022, as mandated in the Energy Independence and Security Act of 2007 under the Renewable Fuels Standard. In the longer term, biofuels derived from algae represent an opportunity to dramatically impact the U.S. energy supply for transportation fuels. The cultivation of algae at a commercial scale could provide sufficient fuel feedstock to meet the transportation fuels needs of the entire United States, while being completely compatible with the existing transportation fuel infrastructure. Further, algal biofuels could prove sustainable for generations—they consume $CO_2$ as a nutrient, have a much higher yield potential than other terrestrial biomass feedstocks, and can be grown with non-fresh water sources without needing to use high-value arable land. However, despite their huge potential, the state of technology for producing algal biofuels is regarded by many in the field to be in its infancy. There is a general consensus that a considerable amount of research needs to be carried out to produce algal-based fuels sustainably and economically enough to be cost-competitive with petroleum-based fuels.

Currently, algae are commercially cultivated in open raceway ponds. Though algae are photosynthetically very efficient and yield 5-10 times more biomass productivity than terrestrial plants, harvesting of algae from the growth medium is still considered to be a significant challenge. In general the concentration of algae in the open ponds is about 0.1-0.5 g/L. Current harvesting costs using a continuous-flow centrifuge have been estimated to be about $1500-2000/ton of dry algal biomass. Any algae-to-fuel strategy, therefore, must consider the energy costs and issues associated with harvesting and dewatering.

Bivalve mollusks are filter-feeding and naturally consume algae as a "bioconverter". These bivalve mollusks feed on the algae biomass and convert algal lipids into molluscan biomass, or discharge the concentrated algal cells as their pseudofeces. Apart from easy harvesting by filtration, pseudofeces have much lower water content than the algae and a more desirable biochemical makeup for lipid extraction (Iritani et al., (1980) *J. Nutrition* 110: 1664-1670). Both the pseudofeces and clam biomass, after removal of shells, can be converted into biocrude or biofuel through advanced thermochemical liquefaction technique without drying the biomass.

*Corbicula* mussels were introduced to North America 50 years ago and are now ubiquitous in rivers and lakes south of 40° latitude (Lauritsen, D. D. (1986) *J. N. Am. Benthol. Soc.* 5: 165-172). They have a short lifespan, high fecundity and fast growth rate (McMahon, R. F. (1982) *Nautilius* 96: 134-141; Ortmann & Grieshaber (2003) *J. Exp. Biol.* 206: 4167-4178). They thrive successfully in systems receiving agricultural and industrial effluent, pollutants, and urban waste (Graczyk et al., (1997) *Parasitol, Today* 13: 348-351). Up to 3,750 individuals per $m^2$ have been recorded in high-nutrient agricultural drainages (McMahon, R. F. (1991) In Thorp & Covich (Eds) *Ecology and Classification of North American Freshwater Invertebrates* Acad. Press, pp 315-399) and densities of 100 to 350 clams/$m^2$ are common in Southeastern streams and rivers (Laurisen & Mozley (1986) *Water Resources Res. Inst. Report* #192, U. N. C.; McMahon, R. F. (1983) In Russell-Hunter W. D. (ed) *The Molllusca*, Acad Press). Native mollusks (Unionidae and Pisidiidae) are less abundant, have lower filtration rates than *C. fluminea*, and typically do not tolerate low oxygen-high nutrient environments (Mattice 1979). *C. fluminea* are preferential filter feeders rather than feeding on detritus (McMahon 1991). These mussels can filter a large range of particle sizes (5-30,000 μm) and are not adversely affected by filtering and feeding on cyanobacteria (Lauritsen, D. D. (1986) *J. N. Am. Benthol. Soc.* 5: 165-172; Wallace et al., (1977) *Arch. fur Hydrobiologie* 79: 506-532), many of which can produce toxins (Carmichael et al., (1992) *J. Appl. Bact.* 72: 445-459). A dense bed of *C. fluminea* filtered the overlying water column (average depth=5.25 m) of a North Carolina river in approximately 1-1.6 days (Lauritsen, D. D. (1986) *J. N. Am. Benthol. Soc.* 5: 165-172) or 1-2 L/hour/individual (Haven & Morales-Alamo (1970) *Biol. Bull.* 139; 248-264; Hildreth & Crisp (1976) *J. marine Biol. Assoc. U.K.* 56: 111-120; Winter, J. E. (1970) In Steele J. H. (ed.) *Marine Food Chains* Oliver & Boyd pp. 196-206).

SUMMARY

Briefly described, the present disclosure provides embodiments of a method of generating a biofuel from an algal-based cultural systems, comprising: culturing a population of mollusks and a population of algal cells in a culture system suitable for maintaining the viability and proliferation of the mollusks and proliferation of the algal cells; allowing the population of the mollusks to isolate a proportion of the algal cells from the cultural system, thereby generating an amount of a molluscan pseudofecal algal-based particulate material; isolating said pseudofecal particulate material from the culture system; and generating a biofuel from the isolated pseudofecal particulate material. The methods can further comprise isolating a lipid material from the tissues of the population of the bivalve mollusks.

In embodiments of this aspect of the disclosure, the population of mollusks is a population of freshwater mollusks, marine mollusks, or estuarine mollusks.

In some embodiments of this aspect of the disclosure, the population of mollusks may comprise at least one freshwater species selected from the group consisting of: a *Corbicula* sp., an *Anodonta* sp., a *Rangia* sp., a *Dreissena* sp., and any combination thereof.

The population of algal cells may comprise at least one species selected from the group consisting of: a *Chlorella* sp., a *Chlamydomonas* sp., a *Scenedesmus* sp., an *Isochrysis* sp., a *Dunaliella* sp., a *Tetraselmis* sp., and a *Nannochloropsis* sp. In some embodiments of this aspect of the disclosure, the population of algal cells comprises at least one species selected from the group consisting of: *Scenedesmus bijuga, Chlorella minutissima, Chlorella sorokinia, Chlamydomonas globosa*, or any combination thereof.

In embodiments of this aspect of the disclosure, the step of isolating the particulate matter from the culture system can be selected from the group consisting of: a filtration method, a sedimentation method, a centrifugation method, a mechanical collection method, and any combination thereof.

In embodiments of this aspect of the disclosure, the step of isolating the lipid matter from the isolated pseudofecal particulate matter can selected from the group consisting of: a solvent extraction method, a steam extraction method, a chemical extraction method, a mechanical extraction method, an enzymatic extraction method, and any combination thereof.

In embodiments of this aspect of the disclosure, the step of isolating lipid material from the mollusk tissues may include a solvent extraction method, a steam extraction method, a chemical extraction method, a mechanical extraction method, or an enzymatic extraction method, or any combination thereof.

In embodiments of this aspect of the disclosure, the method may further comprise the step of generating a biofuel from the lipid material.

In embodiments of this aspect of the disclosure, the methods may further comprise the step of generating a biofuel from the tissues of the mollusks, wherein the generation of a biofuel from the tissues of the mollusks can be by a thermal conversion process.

Another aspect of the disclosure provides for embodiments of systems for generating a biofuel, comprising: a population of a mollusks and a population of algal cells in a culture system configured for maintaining the viability and proliferation of the mollusks and proliferation of the algal cells; a means of isolating an algal-based particulate material from the culture system; and a system for converting the algal-based particulate material into a biofuel. The means of converting the algal-based particulate material into a biofuel can be a thermal conversion process.

In embodiments of this aspect of the disclosure, the population of mollusks can be a population of freshwater mollusks, marine mollusks, or estuarine mollusks such as, but not limited to, at least one freshwater species selected from the group consisting of: a *Corbicula* sp., an *Anodonta* sp., a *Rangia* sp., a *Dreissena* sp., and any combination thereof.

In embodiments of this aspect of the disclosure, the population of algal cells can comprise at least one species selected from the group consisting of: a *Chlorella* sp., a *Chlamydomonas* sp., a *Scenedesmus* sp., an *Isochrysis* sp., a *Dunaliella* sp., a *Tetraselmis* sp., and a *Nannochloropsis* sp. In some embodiments of this aspect of the disclosure, the population of algal cells can comprise at least species selected from the group consisting of: *Scenedesmus bijuga, Chlorella minutissima, Chlorella sorokinia, Chlamydomonas globosa*, or any combination thereof.

In some embodiments of the systems of this aspect of the disclosure, the algal-based particulate material can be molluscan pseudofeces, and the means of isolating an algal-based particulate material from the culture system can be selected from the group consisting of: a filtration system, a sedimentation system, a centrifugation system, a mechanical collection system, and any combination thereof.

Embodiments of the systems of this aspect of the disclosure can further comprise a means of isolating a lipid matter from the isolated algal-based particulate material, said means selected from the group consisting of: a solvent extraction system, a steam extraction system, a chemical extraction system, a mechanical extraction system, an enzymatic extraction system, and any combination thereof.

Embodiments of the systems of this aspect of the disclosure can also further comprise a means of harvesting a population of the mollusks from the culture system and a means of generating a biodiesel from the harvested mollusks, said means selected from the group consisting of: a solvent extraction system, a steam extraction system, a chemical extraction system, a mechanical extraction system, an enzymatic extraction system, a thermal conversion system, and any combination thereof.

BRIEF DESCRIPTION OF THE DRAWINGS

Further aspects of the present disclosure will be more readily appreciated upon review of the detailed description of its various embodiments, described below, when taken in conjunction with the accompanying drawings.

Figure 1:
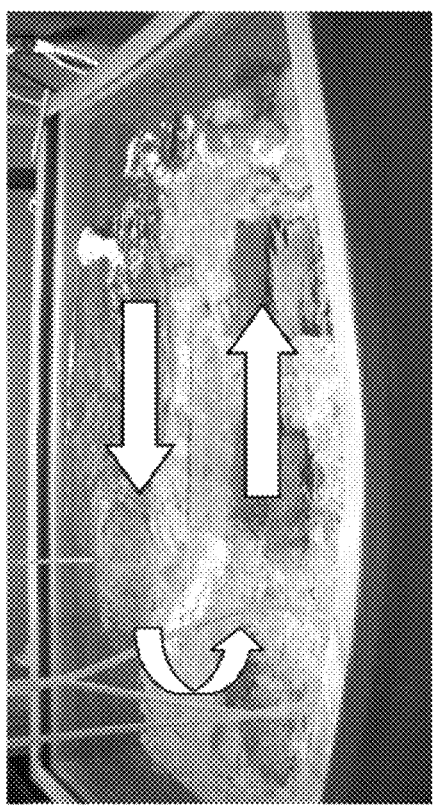
FIG. 1 is a digital photograph showing *Corbicula fluminea* tank system with arrows depicting the circulation produced using a baffle to route the incoming flow.

The drawings are described in greater detail in the description and examples below.

The details of some exemplary embodiments of the methods and systems of the present disclosure are set forth in the description below. Other features, objects, and advantages of the disclosure will be apparent to one of skill in the art upon examination of the following description, drawings, examples and claims. It is intended that all such additional systems, methods, features, and advantages be included within this description, be within the scope of the present disclosure, and be protected by the accompanying claims.

DETAILED DESCRIPTION

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of medicine, organic chemistry, biochemistry, molecular biology, pharmacology, and the like, which are within the skill of the art. Such techniques are explained fully in the literature.

It must be noted that, as used in the specification and the appended claims, the singular forms "a," "an," and "the" include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

As used herein, the following terms have the meanings ascribed to them unless specified otherwise. In this disclosure, "comprises," "comprising," "containing" and "having" and the like can have the meaning ascribed to them in U.S. patent law and can mean "includes," "including," and the like; "consisting essentially of" or "consists essentially" or the like, when applied to methods and compositions encompassed by the present disclosure refers to compositions like those disclosed herein, but which may contain additional structural groups, composition components or method steps (or analogs or derivatives thereof as discussed above). Such additional structural groups, composition components or method steps, etc., however, do not materially affect the basic and novel characteristic(s) of the compositions or methods, compared to those of the corresponding compositions or methods disclosed herein. "Consisting essentially of" or "consists essentially" or the like, when applied to methods and compositions encompassed by the present disclosure have the meaning ascribed in U.S. patent law and the term is open-ended, allowing for the presence of more than that which is recited so long as basic or novel characteristics of that which is recited is not changed by the presence of more than that which is recited, but excludes prior art embodiments.

Prior to describing the various embodiments, the following definitions are provided and should be used unless otherwise indicated.

DEFINITIONS

In describing and claiming the disclosed subject matter, the following terminology will be used in accordance with the definitions set forth below.

The terms "algae" and "algal cells" as used herein refer to a large and diverse group of simple, typically autotrophic organisms, ranging from unicellular to multicellular forms. They are photosynthetic, like plants, and "simple" because they lack the many distinct organs found in land plants. All true algae have a nucleus enclosed within a membrane and chloroplasts bound in one or more membranes. "Microalgae" or "microphytes" (also referred to as phytoplankton, or planktonic algae) are microscopic algae, typically found in freshwater and marine systems. There are 200,000-800,000 species exist of which about 35,000 species are described.

They are unicellular species which exist individually, or in chains or groups. Depending on the species, their sizes can range from a few micrometers (μm) to a few hundreds of micrometers. Microalgae produce approximately half of the atmospheric oxygen and use simultaneously the greenhouse gas carbon dioxide to grow photoautotrophically. The biodiversity of microalgae is enormous and they represent an almost untapped resource. The chemical composition of microalgae is not an intrinsic constant factor but varies over a wide range, both depending on species and on cultivation conditions. Microalgae such as microphytes constitute the basic foodstuff for numerous aquaculture species, especially filtering bivalves. They provide them with vitamins and polyunsaturated fatty acids, necessary for the growth of the bivalves which are unable to synthesize it themselves.

Microalgal species suitable for use in the systems of the present disclosure are freshwater species such as, but not limited to, *Chlorella sorokiniana, Chlorella minutissima, Chlamydomonas globosa*, and *Scenedesmus bijuga*, alone or in mixed cultures thereof, or marine species such as, but not limited to, *Isochrysis galbana* (Phylum Haptophyta, Class Prymnesiophyceae), *Dunaliella tertiolecta* (Phylum Chlorophyta, Class Chlorophyceae), *Tetraselmis suecica* (Phylum Chlorophyta, Class Prasinophyceae), and *Nannochloropsis oculata* (Phylum Heterokontophyta, Class Eustigmatophyceae).

The term "cyanobacteria" as used herein refers to blue-green algae, blue-green bacteria or Cyanophyta, a phylum of bacteria that obtain their energy through photosynthesis. They are a significant component of the marine nitrogen cycle and an important primary producer in many areas of the ocean, but are also found in habitats other than the marine environment; in particular cyanobacteria are known to occur in both freshwater, hypersaline inland lakes, and in arid areas where they are a major component of biological soil crusts.

The term "ANKOMXT10® extraction system" as used herein refers to a specific solvent extraction system for the isolation of lipids (ANKOM Inc., Macedon, N.Y.). The system is based on the solubilization properties of traditional solvents. The ANKOMXT10® Extractor accelerates the process by performing the extraction under pressure at elevated temperatures with reflux/siphon action.

The term "chemical extraction method" as used herein refers to a use of chemicals other than organic solvents to isolate lipids from undesirable components. The Babcock, Gerber and Detergent methods are examples of non-solvent liquid extraction methods for isolation of lipid content, and are well known to one of skill in the art.

The term "enzymatic extraction method" as used herein refers to a method of isolating lipids from undesirable components using enzymes such as hydrolases, proteinases, lipases and the like to break down complexes of polysaccharides, proteins, and lipids to release the desired lipids from the mollusk tissues. Lipids can then be extracted using organic solvents, mechanical methods, or combinations thereof.

The term "mechanical extraction method" as used herein refers to the disruption of mollusk cells by physical methods such as crushing, filtration, sedimentation, and the like, to extract the lipids from the mollusk tissue.

The term "solvent extraction method" as used herein refers to the isolation of lipids using organic solvents and centrifugation methods. The fact that lipids are soluble in organic solvents, but insoluble in water, provides a convenient method of separating the lipid components from water soluble components, such as proteins, carbohydrates and minerals.

The term "steam extraction methods" as used herein refers to heated water extraction which is a technique based on the use of steam heat as an extractant, at elevated temperatures, and at a pressure high enough to convert and maintain lipids in a liquid state.

The terms "aqueous medium," "culture medium" and "cultural medium" as used herein refers to an aqueous medium designed to support the growth of algal cells, and mollusks. For example, and by no means intended to be limiting, an aqueous medium includes a natural water source such as a river, stream, lake, brackish water at the boundary between marine water and freshwater environment, or a marine water source. "Culture media" can include, but are not limited to, artificial aqueous media providing nutrients required by the algae and mollusks, nutrient-rich effluent from agricultural or industrial facilities, land-fill run-off, and the like.

The terms "bivalve mollusk" and "mollusk" as used herein refer to filter-feeding marine and freshwater mollusks belonging to the class Bivalvia. The class contains at least 30,000 known species, including scallops, clams, oysters, and mussels. Some bivalves are epifaunal they attach themselves to surfaces. Others are infaunal and they bury themselves in sediment.

Mollusks including freshwater bivalves such as, but not limited to, *Corbicula fluminea*, the Zebra mussel (*Dreissena polymorpha*), and the Quaga mussel (*Dreissena bugensis*), and marine bivalves such as, but not limited to, the Eastern oyster (*Crassostrea virginica*), *Rangia* (*Rangia cuneata*), the Carolina marsh clam (*Polymesoda caroliniana*), and the Green mussel (*Perna viridis*).

The term "mussel" as used herein is the common name used for members of several families of clams or bivalve mollusks, from saltwater and freshwater habitats.

The term "culture system" as used herein refers to a system of water retaining, filtering, heating/cooling, and circulating systems, and structures that are typically employed in the maintenance of a culture medium under conditions suitable for supporting the viability and reproduction of a desired organism(s).

The term "current" as used herein refers to a flow of water. The current varies spatially as well as temporally within the system, tank or channel dependent upon the flow volume of water, stream gradient, and channel geometrics.

The term "lipid" and "lipid material" as used herein refers to naturally-occurring molecules which includes fats, waxes, sterols, fat-soluble vitamins (such as vitamins A, D, E and K), monoglycerides, diglycerides, phospholipids, and the like. The main biological functions of lipids include energy storage, as structural components of cell membranes, and as important signaling molecules. Lipids may be broadly defined as hydrophobic or amphiphilic small molecules; the amphiphilic nature of some lipids allows them to form structures such as vesicles, liposomes, or membranes in an aqueous environment.

The term "mechanical collection means" as used herein refers to methods that may be used to remove the particulate matter from a surface. Such means may include, but is not limited to, scraping, peeling, scooping, and physically removing using vacuum methods, or other suitable tools.

The term "molluscan feces" as used herein refers to a waste product from a mollusk's digestive tract expelled through the anus (or cloaca) during defecation.

The term "molluscan pseudofeces" as used herein refers to rejected particles, typically wrapped in mucus, and expelled by filter-feeding bivalve mollusks (and filter-feeding gastropod mollusks) without having passed through the digestive tract.

The term "particulate material" means fine, or tiny particles of solid matter that can be suspended in a liquid.

The term "proliferation" as used herein refers to bivalve mollusk and algal reproduction and is used in the contexts of cell development and cell division (reproduction). When used in the context of cell division, it refers to growth of cell populations. Clams incubate fertilized eggs with their inner demibranchs and release their pediveliger larvae which require no secondary host for development. This aspect of some bivalve mollusks permits them to be cultured in tank and pond systems in the absence of a fish host.

The term "substrate" and "substrate layer" as used herein refers to the material used on the tank bottom, or the bottom of the cultural system. This layer can be made of materials such as, but not limited to mud, sand, gravel, pebbles, cobbles, small rocks, and the like. It can affect water chemistry, filtration, and the well-being of the aquarium's inhabitants.

The term "viability" as used herein refers to "capacity for survival" and is more specifically used to mean a capacity for living, developing, or germinating under favorable conditions.

Unless otherwise defined, all other technical and scientific terms used herein have the same meaning as commonly understood by one of ordinary skill in the art of biology. Although methods and materials similar or equivalent to those described herein can be used in the practice or testing of the present invention, suitable methods and materials are described herein.

DESCRIPTION

Embodiments of the present disclosure provides systems and methods for the fixation of atmospheric carbon by algal cultures and harvesting of the algae that can then be used as a source of lipid material for the generation of biodiesel-like fuels. Rather than using harvesting techniques that are high in energy input, use is made of the natural feeding behavior of molluscan bivalves. These animals separate algae, in particular unicellular algae (microalgae) along with other aqueous organisms including, but not limited to, cyanobacter, protozoa, fungal cells and suspended organic detritus, from the aqueous medium by two mechanisms. Firstly, the mesh-like structure of the gills of the clams can act as filtering nets, with oxygen-bearing water passing through the pores of the gill, and particulate matter above a certain size remaining on the 'input' side of the gill. Ultimately, this particulate matter falls from the gill surface, or is actively removed by mucoid secretion and cell flagellar action, and is rejected by the animal. This physically separated and concentrated particulate matter, and aggregations thereof, accumulate as 'pseudofeces.'

The second method of extracting particulate matter from the aqueous environment of the clams is for them to ingest the particles for digestion. As part of this process, the nutrients of the ingested algae and other organic matter can be converted, in part, into the tissues of the clam. Some of the ingested organic material will be converted into lipid-based compounds. Excess ingested material or the waste by-products resulting from the animals metabolism are ejected as fecal matter.

The use of molluscan bivalves as a particulate matter separating mechanism, therefore, provides two routes for gathering lipid-based material for use in biofuel production. The 'pseudofeces' may be collected from the clams' environment by simple techniques such as vacuum sweeping of the substrate of the culture system, which are energetically more economical than if the algae and other organic material was separated by such as a continuous-flow centrifugation process. Additionally, the clams themselves are self-propagating and may be periodically harvested and used as a source of lipid material to supplement the yield of lipid-bearing pseudofeces.

The methods and systems of the present disclosure, therefore, enable harvesting a renewable source of organic material, i.e. algal cells, on a continuous basis and with economy in the input of energy required to concentrate the material prior to conversion to biofuels. Input energy is required merely to maintain culture conditions conducive to the survival, and preferably the proliferation of, the mollusks and for the continual production of algal cells. Propagation of the mollusks themselves can supplement the lipid supply while extending the operating life of the culture systems. The methods and systems of the present disclosure, therefore, advantageously provide a harvesting system for the collection of algal-based sources of lipids, etc, that may be converted into biofuels, compared to alternative systems that harvest algae by energy intensive mechanical methods.

It is contemplated that the systems of the disclosure may be readily adapted for the culturing of a variety of microalgal species alone or in combination, and both freshwater and marine, and for their harvesting by mollusks derived from the corresponding environment, i.e. either freshwater or marine bivalves. The systems and methods of the disclosure may include, but are not limited to, the mussel *Corbicula fluminea*, a species of freshwater clam, an aquatic bivalve mollusk in the family Corbiculidae. They feed primarily on phytoplankton (algae), which they filter from the sandy or muddy bottom of streams, lakes, or canals.

*Corbicula fluminea* is an invasive species that has proved to be harmless to the general freshwater environment. This species is of originally mainly Asian origin and thus it is often commonly called the Asian clam or Asiatic Clam. In Southeast Asia it is known as the prosperity clam or good luck clam. The species has been introduced into many parts of the world, including North America and Europe.

Right after reaching maturity these mollusks produce eggs, followed by sperm. Even later, they produce eggs and sperm simultaneously. They can self-fertilize, and release up to 2,000 juveniles per day, and more than 100,000 in a lifetime. Juveniles are only 1 mm long when discharged, and take one to four years to reach maturity. At this time they are about one centimeter long. Adults can reach a length of about 5 cm.

*C. fluminea*, is a simultaneous hermaphrodite bivalve species with two temperature-dependent spawning peaks, the first in May/June when water temperatures exceed 15° C., and the second in September. The clams incubate fertilized eggs within their inner demibranchs and release their pediveliger larvae which require no secondary host for development. These aspects of *C. fluminea*'s life history allow them to be cultured in tank or pond systems in the absence of a fish host.

In developing the system and methods of the present disclosure, clams of the species *C. fluminea* were collected from the Ocmulgee River (Chattahoochee National Forest, Jackson County, GA) and were used to start an experimental culture such as shown in FIG. 1. It is contemplated, however, that other species of bivalve mollusk can be suitable for use in the systems herein described. For example, species of clams (mussels) from a marine environment may be used, together with marine water, for the culturing and harvesting of algae that more typically belong in the marine environment. It is, therefore, within the scope of the present disclosure for any suitable bivalve clam or mussel to be incorporated into the systems disclosed herein, providing that the aqueous medium and the algal species are compatible.

In one embodiment of the systems of the present disclosure, although it is contemplated that such systems may be scaled according to need, approximately 500 individual clams were maintained in aerated tanks. In this example, the clams were housed in a 480-L tank filled with water from a low-intensity aquaculture pond and aerated with two small diffusers. The pond water could also support a microalgae community that served as a food source for the clams.

Figure 2:
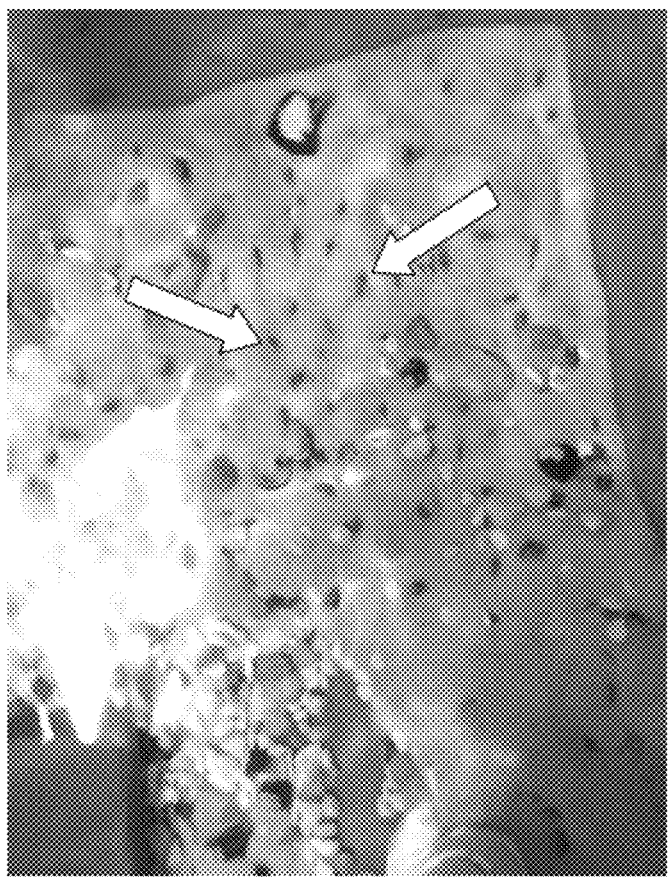
FIG. 2 is a digital photograph showing *C. fluminea* burrowed into substrate for feeding.

The water was circulated through a compartmentalized biofilter system and returned to the tank, where a baffle created a directed current flow. A 7-cm deep mixture of small rocks and sand, simulating to the riverine environment the clams prefer, was used as the substrate, as shown in FIG. 2. The tank received ambient natural light, and light from a halogen light source suspended 0.5 m above the tank (18 h dark-6 h light cycle), to stimulate algal growth. The water temperature was maintained at about 25° C. using an aquarium heater.

One aspect of the present disclosure, therefore, provides embodiments of a method of generating a biofuel from an algal-based cultural system, comprising: culturing a population of mollusks and a population of algal cells in a culture system suitable for maintaining the viability and proliferation of the mollusks and proliferation of the algal cells; allowing the population of the mollusks to isolate a proportion of the algal cells from the cultural system, thereby generating an amount of a molluscan pseudofecal algal-based particulate material; isolating said pseudofecal particulate material from the culture system; and generating a biofuel from the isolated pseudofecal particulate material.

In embodiments of this aspect of the disclosure, the methods can further comprise isolating a lipid material from the tissues of the population of the bivalve mollusks.

In embodiments of this aspect of the disclosure, the population of mollusks is a population of freshwater mollusks, marine mollusks, or estuarine mollusks.

In some embodiments of this aspect of the disclosure, the population of mollusks may comprise at least one freshwater species selected from the group consisting of: a *Corbicula* sp., an *Anodonta* sp., a *Rangia* sp., a *Dreissena* sp., and any combination thereof.

In other embodiments of this aspect of the disclosure, the population of mollusks may comprise at least one marine species selected from the group consisting of: an *Ensis* sp., a *Tagelus* sp., a *Macoma* sp., a *Crassostrea* sp., a *Mya* sp., a *Rangia* sp., a *Polymesoda* sp., a *Perna* sp., and any combination thereof.

In yet other embodiments of this aspect of the disclosure, the population of mollusks may comprise at least one estuarine species selected from the group consisting of: a *Mytilus* sp., an *Anadara* sp., a *Noetia* sp., a *Mercenaria* sp., a *Pectiniae* sp., a *Geukensia* sp., an *Ischadium* sp., a *Petricola* sp., a *Cytropleura* sp., a *Tagelus* sp., and any combination thereof.

In the embodiments of this aspect of the disclosure, the population of algal cells may comprise at least one species selected from the group consisting of: a *Chlorella* sp., a *Chlamydomonas* sp., a *Scenedesmus* sp., an *Isochrysis* sp., a *Dunaliella* sp., a *Tetraselmis* sp., and a *Nannochloropsis* sp.

In some embodiments of this aspect of the disclosure, the population of algal cells comprises at least one species selected from the group consisting of: *Scenedesmus bijuga, Chlorella minutissima, Chlorella sorokinia, Chlamydomonas globosa*, or any combination thereof.

In some other embodiments of this aspect of the disclosure, the population of algal cells may comprise at least one species selected from the group consisting of: *Isochrysis galbana, Dunaliella tertiolecta, Tetraselmis suecica*, and *Nannochloropsis oculata*, or any combination thereof.

In embodiments of this aspect of the disclosure, the step of isolating the particulate matter from the culture system can be selected from the group consisting of: a filtration method, a sedimentation method, a centrifugation method, a mechanical collection method, and any combination thereof.

In embodiments of this aspect of the disclosure, the step of isolating the lipid matter from the isolated pseudofecal particulate matter can selected from the group consisting of: a solvent extraction method, a steam extraction method, a chemical extraction method, a mechanical extraction method, an enzymatic extraction method, and any combination thereof.

In embodiments of this aspect of the disclosure, the step of isolating lipid material from the mollusk tissues may include a solvent extraction method, a steam extraction method, a chemical extraction method, a mechanical extraction method, or an enzymatic extraction method, or any combination thereof.

In embodiments of this aspect of the disclosure, the method may further comprise the step of generating a biofuel from the lipid material.

In embodiments of this aspect of the disclosure, the methods may further comprise the step of generating a biofuel from the tissues of the mollusks, wherein the generation of a biofuel from the tissues of the mollusks can be by a thermal conversion process.

Another aspect of the disclosure provides for embodiments of systems for generating a biofuel, comprising: a population of a mollusks and a population of algal cells in a culture system configured for maintaining the viability and proliferation of the mollusks and proliferation of the algal cells; a means of isolating an algal-based particulate material from the culture system; and a system for converting the algal-based particulate material into a biofuel.

In embodiments of this aspect of the disclosure, the means of converting the algal-based particulate material into a biofuel can be a thermal conversion process.

In embodiments of this aspect of the disclosure, the population of mollusks can be a population of freshwater mollusks, marine mollusks, or estuarine mollusks.

In embodiments of this aspect of the disclosure, the population of mollusks can comprise at least one freshwater species selected from the group consisting of: a *Corbicula* sp., an *Anodonta* sp., a *Rangia* sp., a *Dreissena* sp., and any combination thereof.

In some embodiments of this aspect of the disclosure, the population of mollusks can comprise at least one marine species selected from the group consisting of: an *Ensis* sp., a *Tagelus* sp., a *Macoma* sp., a *Crassostrea* sp., a *Mya* sp., a *Rangia* sp., a *Polymesoda* sp., and a *Perna* sp., and any combination thereof.

In other embodiments of this aspect of the disclosure, the population of mollusks can comprise at least one estuarine species selected from the group consisting of: a *Mytilus* sp., an *Anadara* sp., a *Noetia* sp., a *Mercenaria* sp., a *Pectiniae* sp., a *Geukensia* sp., an *Ischadium* sp., a *Petricola* sp., a *Cytropleura* sp., a *Tagelus* sp., and any combination thereof.

In embodiments of this aspect of the disclosure, the population of algal cells can comprise at least one species selected from the group consisting of: a *Chlorella* sp., a *Chlamydomonas* sp., a *Scenedesmus* sp., an *Isochrysis* sp., a *Dunaliella* sp., a *Tetraselmis* sp., and a *Nannochloropsis* sp.

In some embodiments of this aspect of the disclosure, the population of algal cells can comprise at least species selected from the group consisting of: *Scenedesmus bijuga, Chlorella minutissima, Chlorella sorokinia, Chlamydomonas globosa*, or any combination thereof.

In embodiments of the systems of this aspect of the disclosure, the culture system can comprise an aqueous medium and a substrate layer, said substrate layer selected from the group consisting of: rocks, gravel, sand, mud, and any combination thereof.

In embodiments of the systems of this aspect of the disclosure, the aqueous medium can flow relative to the mollusks.

In some embodiments of the systems of this aspect of the disclosure, the algal-based particulate material can be molluscan pseudofeces, and the means of isolating an algal-based particulate material from the culture system can be selected from the group consisting of: a filtration system, a sedimentation system, a centrifugation system, a mechanical collection system, and any combination thereof.

Embodiments of the systems of this aspect of the disclosure can further comprise a means of isolating a lipid matter from the isolated algal-based particulate material, said means selected from the group consisting of: a solvent extraction system, a steam extraction system, a chemical extraction system, a mechanical extraction system, an enzymatic extraction system, and any combination thereof.

Embodiments of the systems of this aspect of the disclosure can also further comprise a means of harvesting a population of the mollusks from the culture system and a means of generating a biodiesel from the harvested mollusks, said means selected from the group consisting of: a solvent extraction system, a steam extraction system, a chemical extraction system, a mechanical extraction system, an enzymatic extraction system, a thermal conversion system, and any combination thereof.

The specific examples below are to be construed as merely illustrative, and not limitative of the remainder of the disclosure in any way whatsoever. Without further elaboration, it is believed that one skilled in the art can, based on the description herein, utilize the present disclosure to its fullest extent. All publications recited herein are hereby incorporated by reference in their entirety.

It should be emphasized that the embodiments of the present disclosure, particularly, any "preferred" embodiments, are merely possible examples of the implementations, merely set forth for a clear understanding of the principles of the disclosure. Many variations and modifications may be made to the above-described embodiment(s) of the disclosure without departing substantially from the spirit and principles of the disclosure. All such modifications and variations are intended to be included herein within the scope of this disclosure, and the present disclosure and protected by the following claims.

The following examples are put forth so as to provide those of ordinary skill in the art with a complete disclosure and description of how to perform the methods and use the compositions and compounds disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. In an embodiment, the term "about" can include traditional rounding according to significant figures of the numerical value.

EXAMPLES

Example 1

Analytical methods: The ANKOMXT10® Extraction System (Ankom Technology, Macedon, N.Y.), was used to determine the crude fat content of the clam flesh and pseudofeces. Approximately 100 mg of the dried filtered Corbicula pseudofeces from each Partitioned Aquaculture System (PAS) tank (R=3) was weighed, placed in tared, labeled filter bags, sealed and dried at 102° C. for 30 minutes to minimize the effects of rehydration during weighing. The samples were secured inside the Teflon insert. Two hundred ml of hexane was added to the extraction vessel and the Teflon insert was placed inside the vessel. An additional 150 ml of hexane was then added to the insert. The sample was automatically extracted and rinsed inside this vessel. After extraction the samples were dried at 102° C. for 30 minutes, cooled in a desiccant pouch and reweighed. The reduction in weight after extraction is recorded as the crude fat content.

Approximately 1 g of the dried Corbicula tissues from each PAS (R=3) was weighed, placed in tared, labeled filter bags, sealed and dried at 102° C. for 30 minutes to minimize the effects of rehydration during weighing. The samples were secured inside the Teflon insert. Two hundred ml of hexane was added to the extraction vessel and the Teflon insert was placed inside the vessel. An additional 150 ml of hexane was then added to the insert. The sample is automatically extracted and rinsed inside this vessel. After extraction the samples were dried at 102° C. for 30 minutes, cooled in a desiccant pouch and reweighed. The reduction in weight after extraction is recorded as the crude fat content.

Total lipid analysis for pseudofeces was adapted from (Kates & Volcani (1966) *Biochim. Biophys. Acta* 116: 264-278, incorporated herein by reference in its entirety). Ten ml of a sample of pseudofeces was filtered using 2.5 cm Whatman GF/C filters, rinsed with 0.65 M ammonium formate solution and stored at −80° C. For extraction, the filters were thawed and homogenized in a glass mortar with 5 mL methanol:chloroform:water (2:1:0.8, v:v:v). The extract was then transferred to a 10 mL glass stoppered centrifuge tube and centrifuged at about 1,000×g for 10 min at room temperature. The extract was then made up to 5.7 mL with fresh methanol:chloroform:water, and 1.5 mL chloroform followed by 1.5 mL water were added and stirred. After partial phase separation, the sample was again centrifuged for 5 min to complete phase separation. The green bottom chloroform layer was carefully transferred to a dry, preweighed 4 mL glass vial and a few drops of toluene added to remove any unintentionally transferred aqueous phase, and the extract was then dried with $N_2$. The vials were then stored over KOH pellets overnight in a vacuum desiccator before weighing.

Biomass, as total dry weight, was determined by filtering 10-50 mL of culture onto pre-weighed 2.5 cm Whatman GF/C glass fiber filters (before weighing the filters were washed with deionized water and dried for 24 hr at 70° C.). Ash-free dry weight was determined by ashing the filters at 450° C. for 7 hr and then cooling overnight in the vacuum desiccator before weighing.

Example 2

Determination of the mass of algae removed from the water column by *C. fluminea* and algal density effect on the rate of removal: Twenty-four hours prior to initiating the experiments described in Example 1 above, 9 randomly-selected clams were removed from the holding system and placed in filtered water to ensure that any residual algal or other food particles present in the clam's digestive tract that may impact the analyses were negligible.

The clams were weighed (average wt=3.7305 g) and individually placed in 1-L beakers filled with filtered water. Three additional beakers with no clams served as controls to account for algal particles settling. A mixed algal culture, including *Scenedesmus bijuga, Chlorella minutissima*, and *Chlamydomonas* globosa (initial algal concentration: 0.02 g/L) was centrifuged at 3700 rpm until a paste-like consistency was obtained. The algal paste was added to the beakers accordingly to achieve low (0.02 g algal paste/L), medium (0.1 g algal paste/L), and high (0.2 g algal paste/L) initial concentrations. Before the addition of the clams the algal paste was stirred vigorously for 1 minute to suspend the cells and break up any aggregates. Biomass samples were taken at start, 1 and 3 hours. Each beaker was observed hourly to determine if the clams were feeding (shell open, siphons extended) and for the presence of pseudofeces.

Figure 5:
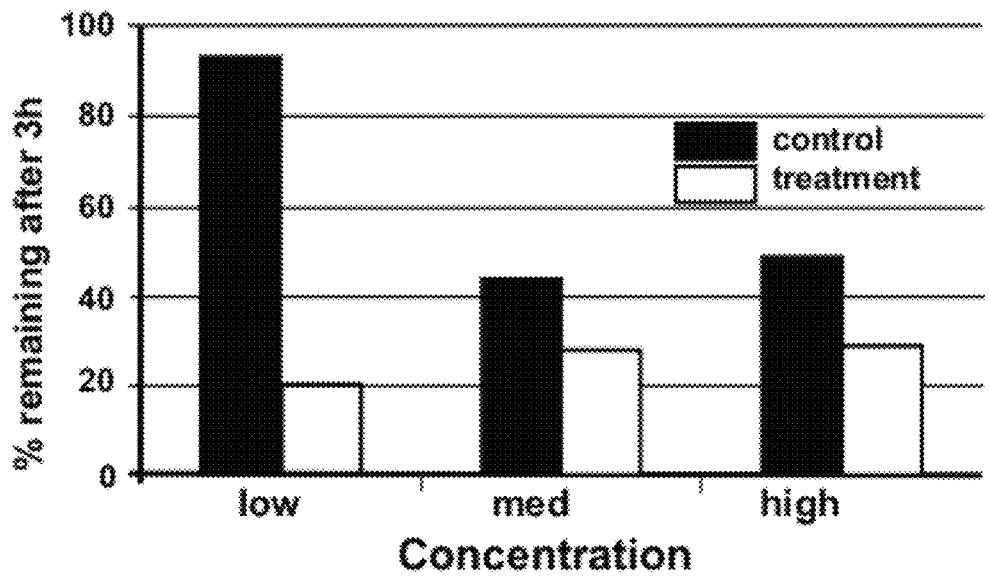
FIG. 5 is a graph showing the percent of algal biomass, averaged for each concentration, remaining after 3 hours.
Figure 6:
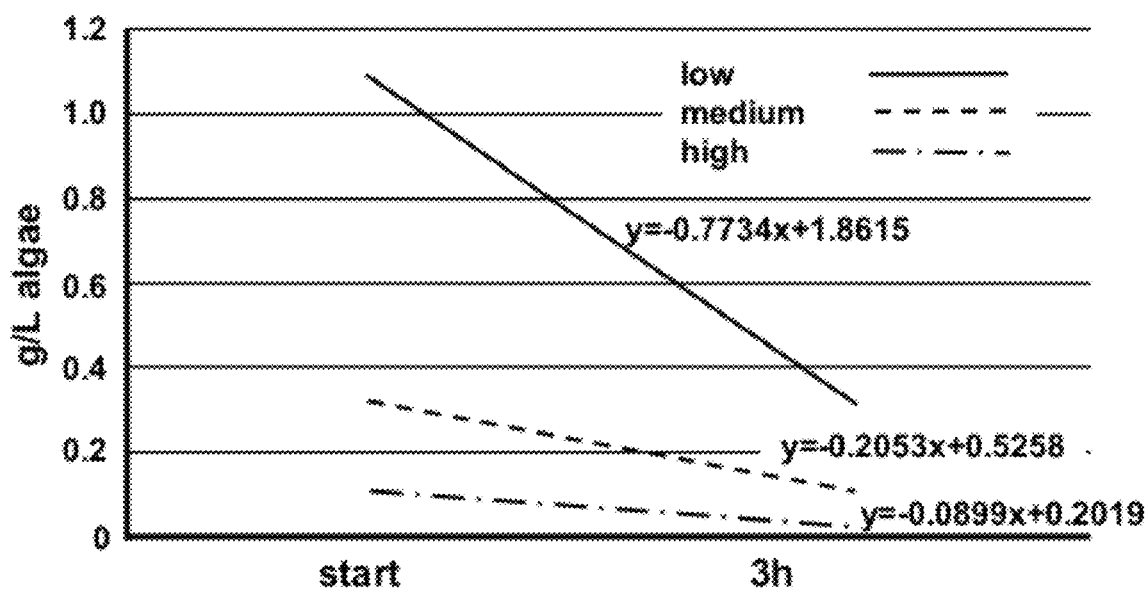
FIG. 6 is a graph showing the average change in algal biomass, expressed as g/L remaining over time, presented for each concentration viz. low, medium, and high.

The clams reduced algal biomass at all concentrations, but the percent of total biomass removed was highest at the lowest concentration of algal suspension fed to the clams as shown in FIG. 5. However, the rate at which the clams removed algae was faster at the highest concentration as shown in FIG. 6. The clams were observed feeding immediately and pseudofeces were present at 1 h. The clams removed 73.8% of the total starting biomass in the lowest concentration treatment, 15.8% in the treatment with medium concentration, and 19.8% at the treatment with highest concentration. Algal settling was adjusted for in each treatment by subtracting the biomass reduction measured in the corresponding control. Algae began to form aggregates on the clams' mantle in the treatments with medium and higher concentration of algae after approximately 1 h, which may have interfered with filtration.

Example 3

Algal biomass removal by *C. fluminea*; strain comparison among three test strains of algae: *Scenedesmus bijuga, Chlorella minutissima*, and *Chladymonas globosa*: Twenty-four hours prior to use, 9 randomly-selected clams were removed from the holding system and placed in clean, filtered water (Laurisen & Mozley (1986) *Water Resources Res. Inst. Report* #192, U. N. C.). The clams were weighed (avg=3.76 g) and individually placed in 1-L beakers filled with filtered water. Water temperature was maintained at 24° C. Three control beakers (no clam) were provided for each strain. Each beaker was inoculated with 30 ml from a culture of *S. bijuga* (group A, R=3), *C. globosa* (group B, R=3), and *C. minutissima* (group C, R=3). The beakers were stirred vigorously for 1 minute, before the addition of the clams to suspend the algae and break up any aggregates.

Ten ml of inoculate from each strain was reserved for biomass analyses and 50 ml was collected from each beaker at 1, 3, and 6 hr for biomass analyses. The beakers were observed hourly to determine if clams were feeding and for the presence of pseudofeces.

Figure 7:
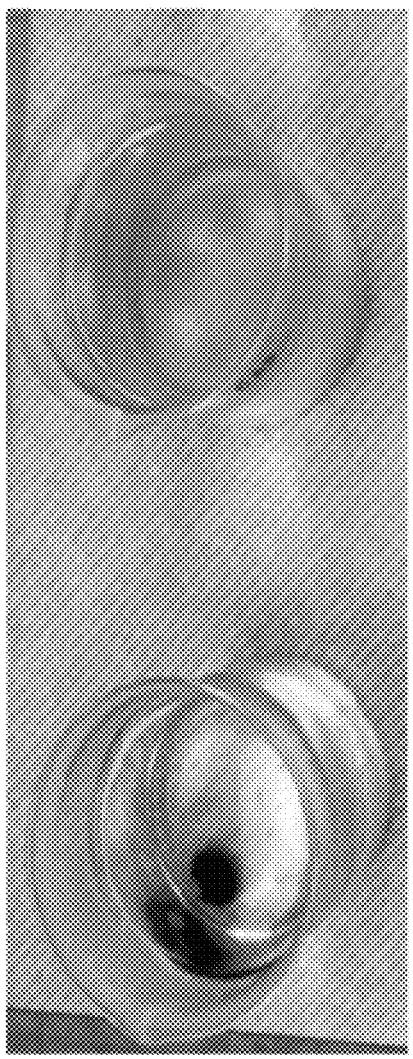
FIG. 7 is a digital photograph showing that after 1 hr from the addition of the alga *S. bijuga*, water clarity markedly increased in the treatment with clams versus control.
Figure 8:
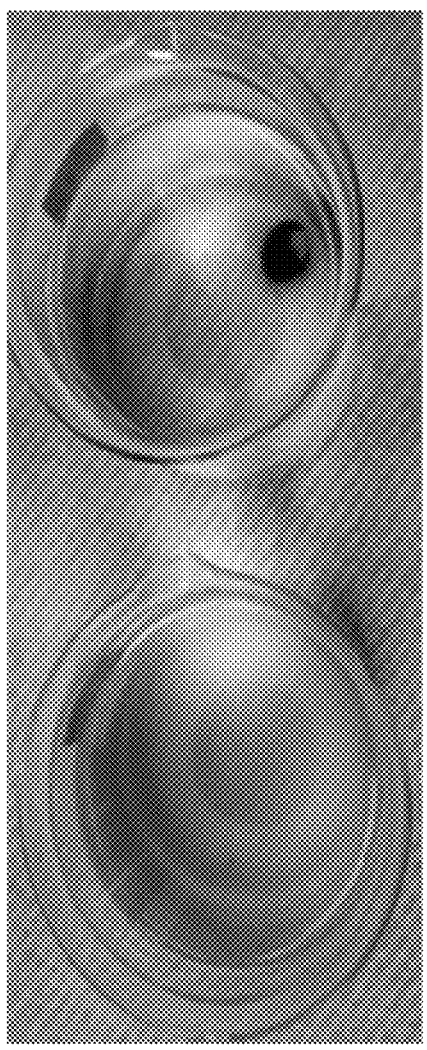
FIG. 8 is a digital photograph showing that after 1 hr from the addition of the alga, *Chlorella minutissima*, water clarity increased in the treatment with clams versus control.

The reduction in algal biomass was visible after 1 hr in the *S. bijuga*, and *C. minutissima* treatments, as shown in FIGS. 7 and 8. The clams were observed feeding in each treatment immediately following the addition of algae and pseudofeces were present after approximately 1.5 h.

Figure 9:
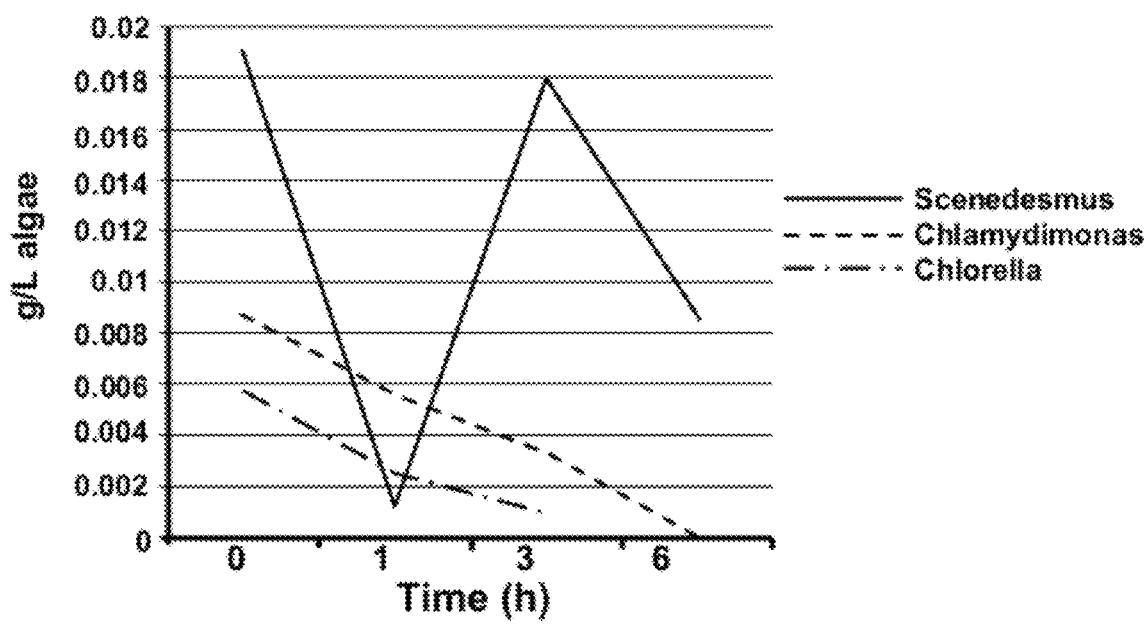
FIG. 9 is a graph showing algal biomass (g/L) remaining over time for each treatment. *C. globosa* is represented by 2 replicates.

The biomass removal rate was initially faster for *S. bijuga* but biomass increased at the 3 hr time point before decreasing again at 6 h, as shown in FIG. 9. This was likely because the filter was contaminated with debris during processing; the original sample contained resuspended pseudofeces, or sand particles from the clam. A study which fed $^{14}C$-labeled algae to *C. fluminea* found that 1 hour is the time period at which no label was respired or excreted (Lauritsen, D. D. (1986) *J. N. Am. Benthol. Soc.* 5: 165-172). If excreted particles (i.e. pseudofeces) interfered with determining biomass reduction after 1 h, then this time point may represent the most accurate estimation of algal biomass reduction by *C. fluminea*, see FIG. 9.

Figure 10:
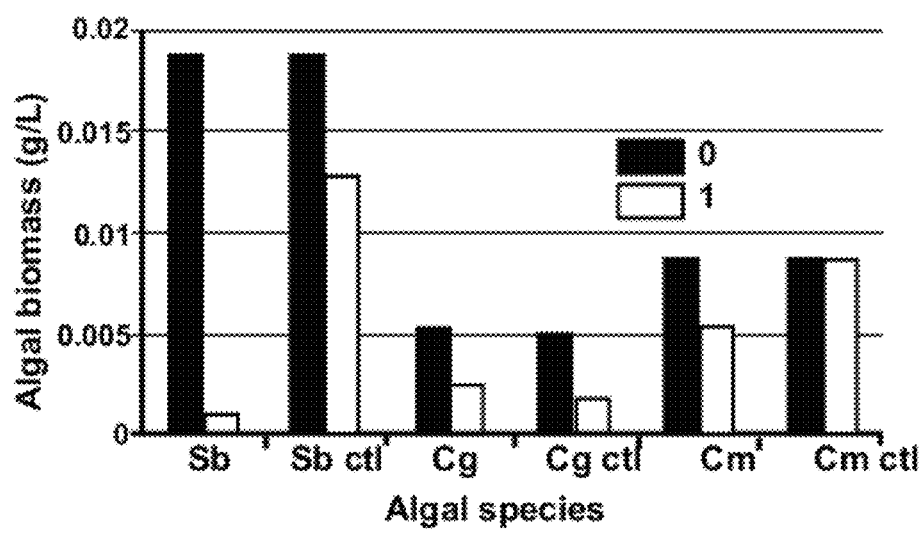
FIG. 10 is a graph showing the algal biomass (g/L) present at time 0 and the biomass remaining after 1 hr for 3 different species, each of which includes a treatment with clams or control (no clams).
Figure 11:
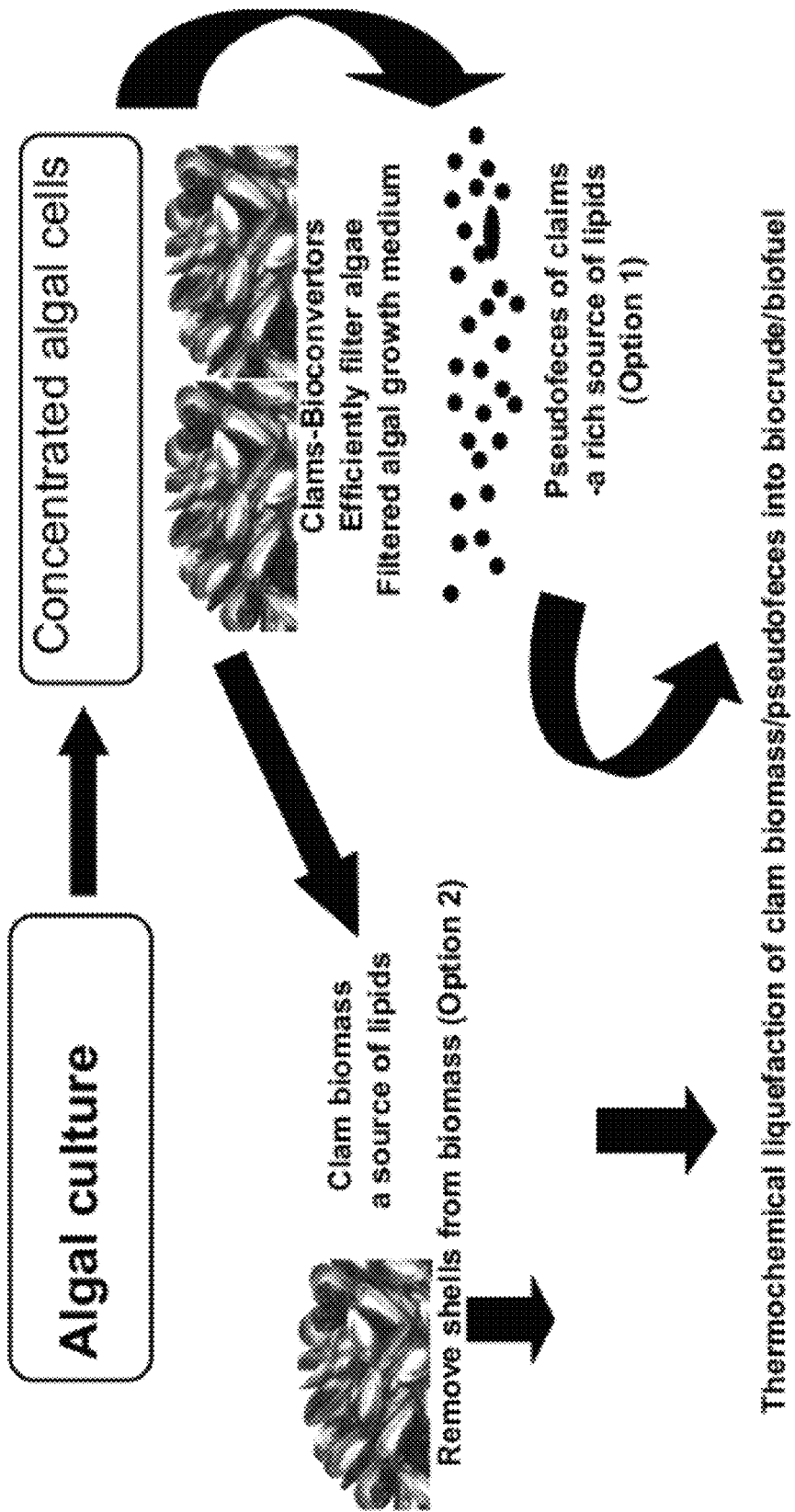
FIG. 11 schematically shows a flow chart of a method of harvesting mollusk feces for biofuels manufacture.

After 1 h, 62.2% *S. bijuga* biomass, and 36.4% *C. minutissima* biomass were removed by the clams (algal settling was adjusted for in the same manner as Example 1), see FIG. 10. Biomass reduction of *C. globosa*, when adjusted for settling in the control, was negligible at this time point. *C. fluminea* were found to assimilate *Chlorella* sp. at an intermediate rate (33%) when compared to other algae, such as *Anabaena* sp. (85%) (Laurisen & Mozley (1986) *Water Resources Res. Inst. Report* #192, U.N.C.). This study, which did not assess *Scenedesmus* sp., found that *Chlorella* is filtered more quickly. After 6 h, *C. minutissima* was the only species which was virtually eliminated (99.5% reduction) by the clams.

Example 4

Figure 3:
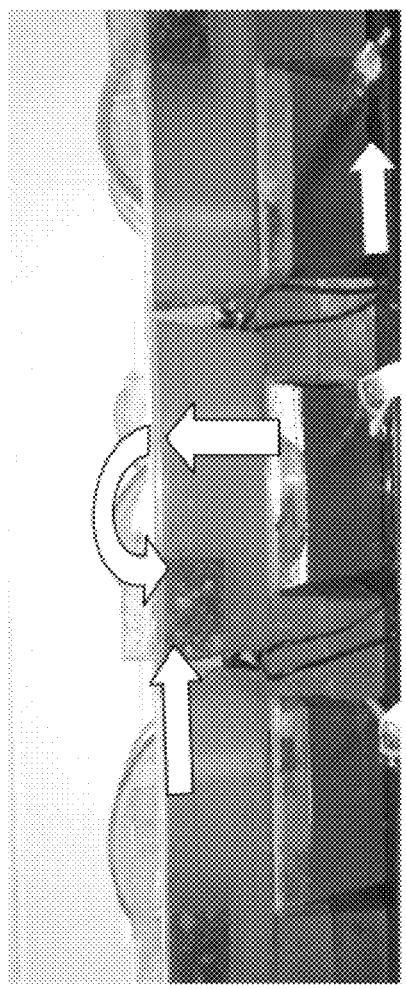
FIG. 3 is a digital photograph showing a recirculating system that avoids the resuspension of pseudofeces while maintaining the clams' ability to feed on algae.
Figure 4:
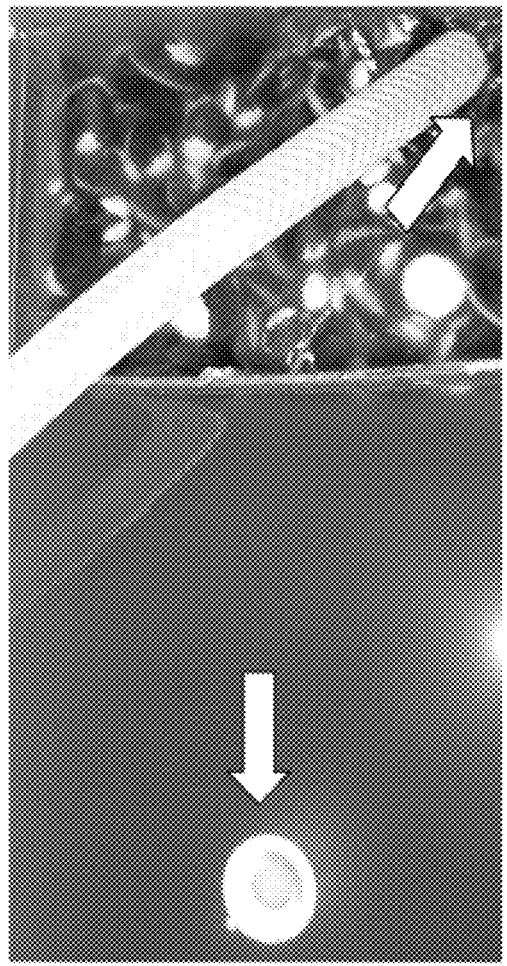
FIG. 4 is a digital photograph showing a view of the upper compartment of a tank system where algae and water were continuously returned from the lower reservoir to the clams before slowly seeping out of the clams' perforated compartment and draining back down.

Comparing lipid levels between *C. fluminea* and their pseudofeces in small-scale recirculating systems: The recirculating systems were constructed from 2 (4 L) plastic boxes as shown in FIG. 3. The top box drained to the bottom via a standpipe and the water and algae were returned across the clams, with a small aquarium pump, as shown in FIG. 4. To minimize the resuspension of pseudofeces, the clams were placed in a small, perforated compartment within the system. Small aquarium heaters placed in each system maintained the water temperature at 26° C. during the 6 h example.

Approximately 1.5 kg of *Corbicula* were removed from the culture 24 hr prior to the example and held in clean filtered water maintained at 24° C. At the start of the example, 0.5 kg of clams were placed into each system (Average=504.93) and 3 L of a mixed algal culture, including *S. bijuga, C. minutissima*, and *C. globosa*, was added to each system. Fifty ml of the culture used to inoculate each system was reserved for biomass determination. The clams were observed throughout the example for signs that they were feeding and for the presence of pseudofeces. A 50 ml biomass sample was taken from the bottom portion of each system at 6 hr when the example ended.

The pseudofeces were collected from each system by filtering the water through a 125 μm mesh filter. The pseudofeces was re-suspended in a small amount of water and stored in a cooler. Microfiber filters were labeled, dried in a 60° C. oven and masses were recorded. The pseudofeces suspensions were filtered through the dried filters. These filters were placed in a 60° C. oven over night. The mass of the dried filters and pseudofeces were then recorded.

The clam tissues were removed from the shells and the tissues were lyophilized. After the clams were completely dry, they were stored at −20° C. for lipid analysis.

The initial algal biomass (0.3 g/L) was on average, reduced by 64.3% after 6 h. Because the water and algae are constantly circulated in these systems settling can be assumed to be negligible (Hildreth and Crisp 1976; Petrocelli et al., (1977) In Evans & Muramatsu (eds) *Radiotracer Techniques & Applications Dekker*, inc. pp 921-968). Using the ANKO-MXT10® method, it was determined that the clams' flesh contained 10.9% lipids (dry wt) and their pseudofeces contained 1.9% lipids (dry wt). The actual percentage of lipids in the tissues and pseudofeces was likely underestimated because of limitations of the drying processes. Preliminary data was collected in preparation for these examples using Kates and Volcani's (1966) method of lipid analysis. This method is commonly used to determine algal lipid content and is more suitable for samples of a smaller mass, such as pseudofeces, than the ANKOMXT10® extraction. Pseudofeces collected from clams (n=30) fed with a mixed culture of algae were evaluated using this method and were found to contain 14.5% lipids.

Example 5

Clam flesh was obtained from fisheries department, Warnell School, UGA. The feedstock was refrigerated till further use. The original feedstock had a greater than 95% moisture content that was reduced to about 80% by placing on a screen. The feedstock thus obtained was analyzed for initial moisture content before liquefaction by an oven drying method at 105° C. for 2 hrs.

Figure 12:
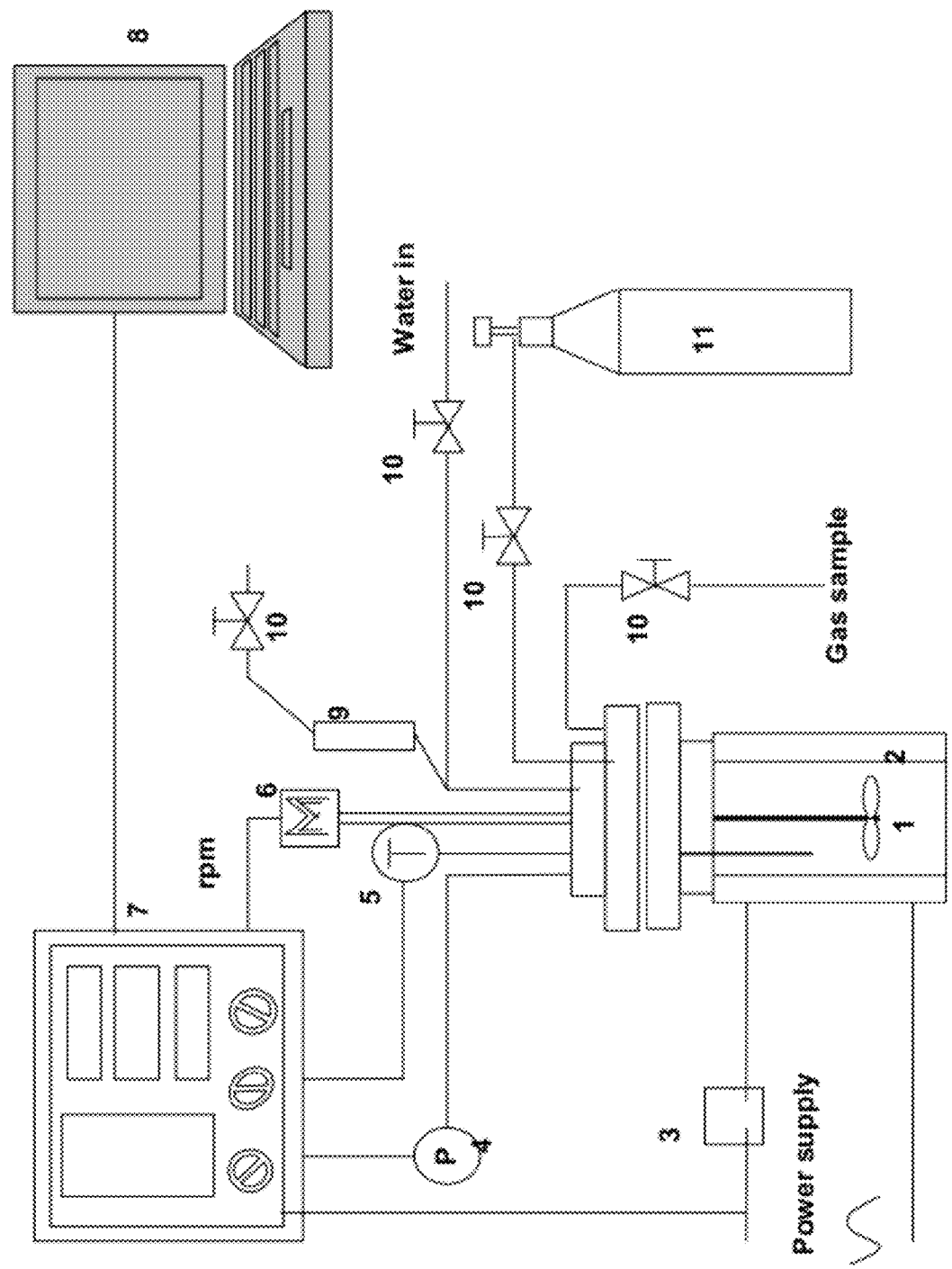
FIG. 12 shows a schematic diagram of a TCC reactor apparatus. 1, Reactor; 2, Heater unit; 3, Power relay; 4, Pressure sensor; 5, Thermocouple; 6, Stirrer assembly; 7, Controllers; 8, Computer; 9, Condenser for liquid sampling; 10, Valves; 11, $N_2$ gas cylinder.

Thermochemical liquefaction experiments were carried out in batch type stirred reactor apparatus (Parr Instruments Co. Moline, Pa.). The thermochemical conversion (TCC) experimental apparatus consisted of a 1.8 L high pressure cylindrical reactor equipped with real-time sampling ports (both gas and liquid samples), process controllers, and a data logger, as shown in FIG. 12. The liquefaction experiments were conducted in a nitrogen atmosphere at two levels of organic solid concentrations in the slurry (4%, and 20%), and at two levels of temperatures, 300° C. and 350° C. (±3° C.) for a 60 mins reaction time. The reaction time was from where the sample temperature reached the desired set temperature. Bio-oil and gas yield, properties of bio-oil and gas were monitored.

Figure 13:
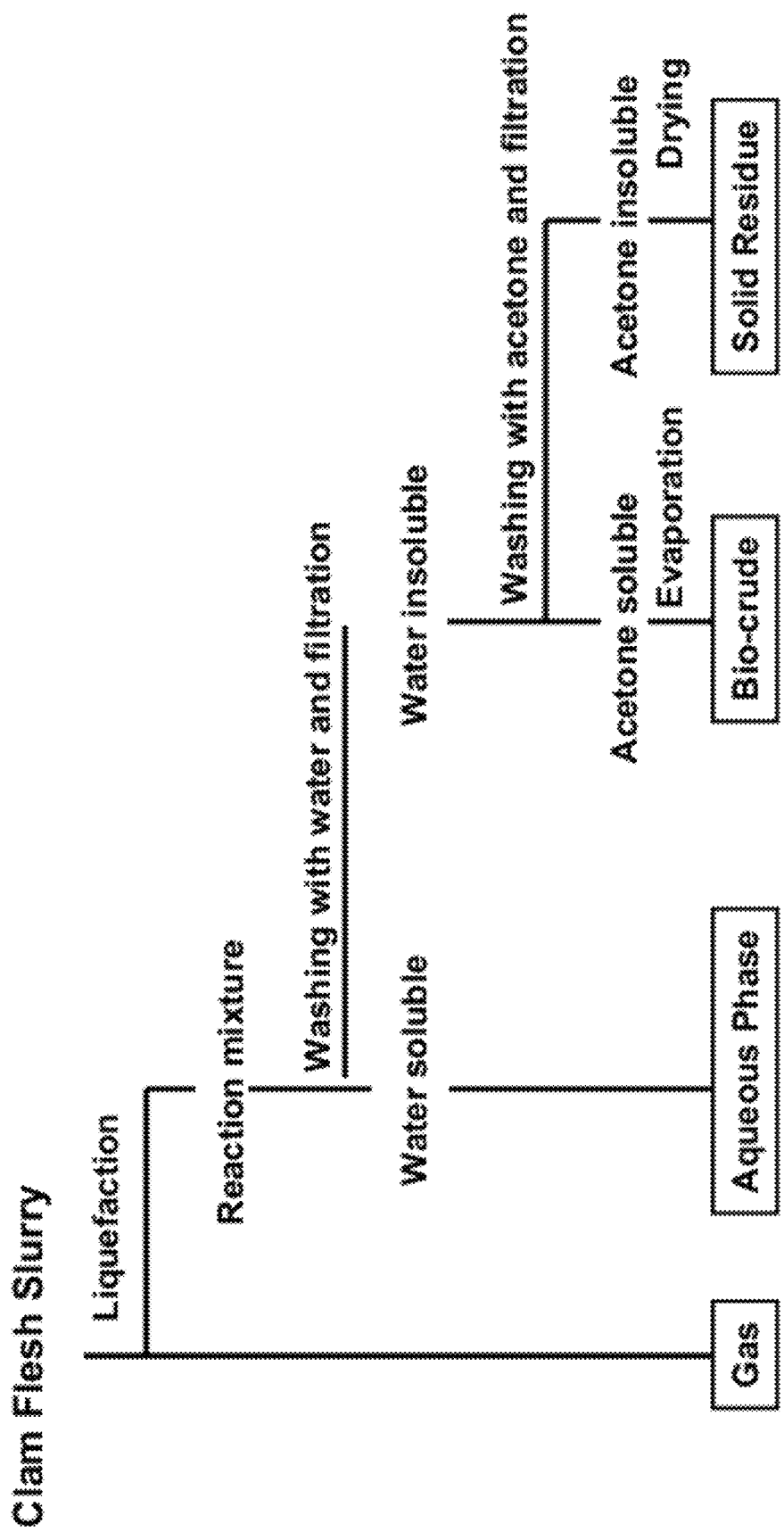
FIG. 13 schematically shows a flow chart for the procedure for the separation of products from the reaction mixture

Clam flesh-water slurry (100 g) was placed inside the reactor, and the reactor sealed, purged with nitrogen to remove air, and pressurized to 2 MPa to prevent the vaporization of water during the reaction. A stirring speed of 300 rpm was maintained for all the runs. At the end of the reaction the reactor was cooled by tap water by a temperature controlled solenoid valve system. Gases were sampled into a gas bag and analyzed by a gas chromatograph (Agilent micro GC 300A). The gas fraction was determined by measuring the weight difference of the reactor and contents before and after the experiment and assuming no loss of products during reaction. The bio-crude, solid residue and aqueous phase were separated from the reaction mixture by the procedure schematically shown in FIG. 13.

Moisture, ash, volatiles and fixed carbon content of the samples were analyzed by the ASTM method D5142 using LECO TGA-701 proximate analyzer (Leco Corp., MI, USA). Analysis of biomass and product samples were also performed for measuring the elemental carbon, hydrogen, nitrogen and sulfur by the ASTM method D5291 using the LECO CHNS-932 analyzer (Leco Corp., MI, USA). Protein and lipid contents were analyzed. Gas samples and the bio-crude samples were analyzed by gas chromatograph-mass spectrometer (GC-MS), 6890 GC with HP 5973 mass detector (Agilent Tech. Santa Clara, Calif., USA). Higher heating values (HHV) of solid and liquid samples have been measured by a bomb calorimeter.

Material balance on the conversion process had been conducted to evaluate the carbon conversion efficiency. The yield of each fraction was defined as:

$$\text{Bio-crude yield (\%)} = \frac{\text{Weight of bio-crude}}{\text{Weight of starting biomass}} \times 100$$

Similarly gaseous products yield and solid residues yield were found from the weight of gas (difference of reactor weight before and after the reaction) and weight of the solids on the initial biomass weight basis.

Example 6

Thermochemical liquefaction of clams: Chemical and compositional analyses of clam biomass are presented in the Table 1. The clam flesh biomass has higher dry basis volatile matter content, but has a very low level of fixed carbon than most other plant biomass feedstocks. It has a considerably higher amount of energy value, 20.83 KJ/kg indicating the clam-based biomass can be utilized for energy recovery employing suitable conversion process.

TABLE 1

| Chemical analysis of clam flesh (Dry weight basis) | |
|---|---|
| Proximate analysis (%) | |
| Volatiles | 86.30 ± 0.73 |
| Ashes | 10.90 ± 0.28 |
| Fixed carbon | 5.87 ± 0.44 |
| Ultimate analysis (%) | |
| C | 43.29 ± 0.97 |
| H | 7.56 ± 0.25 |
| N | 9.53 ± 0.54 |
| S | 0.68 ± 0.10 |
| Higher heating value, (HHV) in MJ/kg | 20.63 ± 0.23 |
| Biochemical composition, (%) | |
| Protein | — |
| Lipids | — |
| Carbohydrates | — |

(Samples were analyzed in triplicates)

The average bio-oil yield from the three runs was reported to be 14.67%. The bio-oil derived from the thermochemical liquefaction of the clam flesh was of dark brown in color and light smoky in odor. The oil was thick and was sticky in nature. Physical and chemical properties of the clam flesh derived bio-oil has been shown in Table 2.

TABLE 2

| Properties of clam flesh bio-oil | |
|---|---|
| Bio-oil yield, % | 14.67 |
| Gaseous yield, % | — |
| Solids yield, % | |
| *Others | |
| Appearance | Dark brown |
| Smell | Smoky |

TABLE 2-continued

Properties of clam flesh bio-oil

| | |
|---|---|
| Specific gravity | 1.09 ± 0.02 |
| pH | 8.72 ± 0.02 |
| Ultimate analysis (%) | |
| C | 63.67 ± 1.95 |
| H | 10.85 ± 0.28 |
| N | 5.16 ± 0.13 |
| S | 0.57 ± 0.01 |
| Higher heating value, (HHV) in MJ/kg | — |

(*Balance on initial biomass basis)

Example 7

Figure 19:
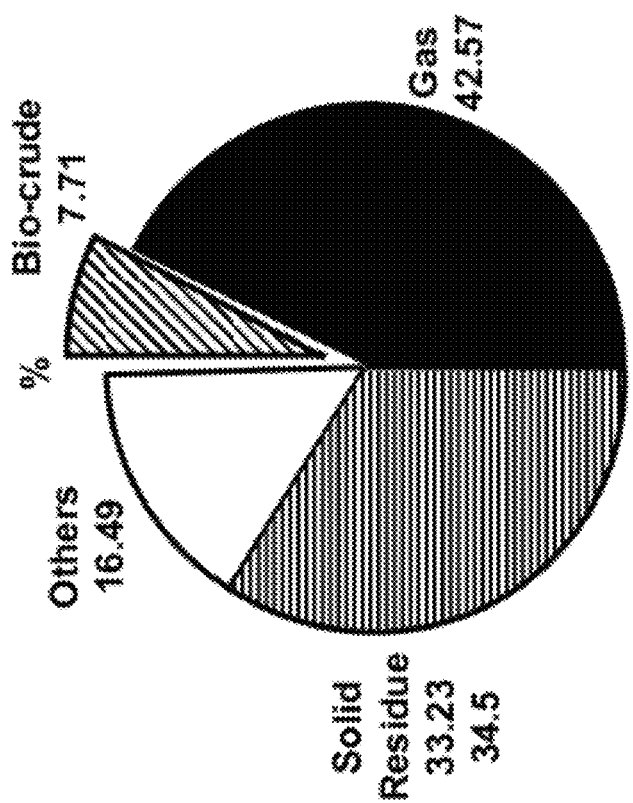
FIG. 19 shows distribution of yield of different products from the non-catalytic liquefaction of *spirulina platensis* and mixed algae at 10% organic solid concentration processed at 350° C. temperature for 60 minutes reaction time.
Figure 19:
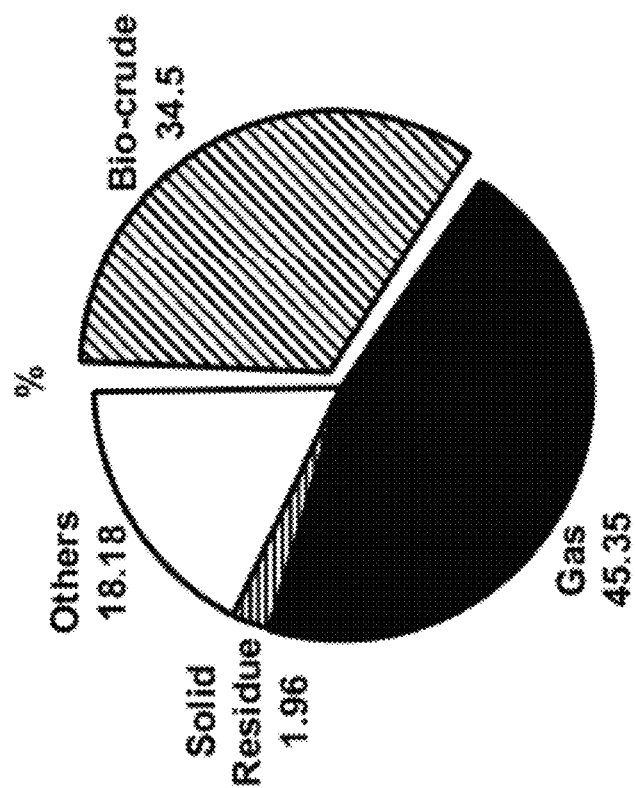

FIG. 19 shows distribution of yield of different products from the non-catalytic liquefaction of *spirulina platensis* and mixed algae at 10% organic solid concentration processed at 350° C. temperature for 60 minutes reaction time. The higher solid residue yield and lower bio-crude yield in case of mixed algae were due to significantly higher ash content and lower protein and lipid content than that of *Spirulina platensis* (Table 1).

Example 8

Biocrude properties: The biocrude produced from liquefaction of clam flesh biomass had higher carbon and hydrogen content and lower oxygen content (Suzuki et al., 1986) than that of the original feed stocks (Table 3). It contained an energy value (30-36 MJ/kg) close to that of petroleum fuel (42 MJ/kg). The bio-crude had an alkaline pH (9.33±0.13), 5-9% water content and an average viscosity of 25 centistokes. A qualitative GC-MS analysis of bio-crude samples has revealed the presence of gasoline range compounds such as decanoic acids, carboxylic acids, alkanes ($C_5$, $C_7$, $C_{16}$), alcohol, amines, ketones, phenol, indole, cyclohexane, toluene, benzene, and methyl esters.

TABLE 3

Elemental CHNS analysis pH analysis of bio-crude from clam feedstock

| | Feedstocks used | | | | |
|---|---|---|---|---|---|
| | C | H | N | S | O |
| Clam oil (300° C.) | 68.31 ± 1.07 | 8.36 ± 0.13 | 6.23 ± 0.11 | 0.65 ± 0.03 | 16.45 ± 0.09 |
| Clam oil (350° C.) | 72.97 ± 1.40 | 8.55 ± 0.09 | 6.53 ± 0.16 | 1.21 ± 0.00 | 10.74 ± 0.13 |

TABLE 4

Major chemical compositions of bio-oil obtained from clam flesh liquefaction

| No. | RT (min) | Name of compound | Area (%) |
|---|---|---|---|
| 1 | 7.40 | Hexane, 2,3-dimethyl Cyclopentane, 1,3-dimethyl-,cis-2-Heptane | 1.44 |
| 2 | 21.21 | Heptadecane | 0.73 |
| 3 | 22.23 | 6-(2-Formylhydrazino)-N,N'-bis (isopropoyl)-1,3,5-triazine, 2,4 diamine | 2.24 |
| 4 | 23.66 | Benzaldehyde | 1.90 |
| 5 | 24.188 | Hexadecanoic acid, methyl ester Pentadecanoic acid, 14-methyl etser | 2.79 |
| 6 | 26.07 | Cobalt, .eta.-5-indenyl, .eta.-5-penamethyl cyclopentadienyl phenol | 5.57 |
| 7 | 26.20 | 9.12-Octadecadienoic acid (Z,Z)-methyl ester | 1.97 |
| 8 | 26.26 | 6-Octadecadienoic acid-methyl ester (Z) 11-Octadecadienoic acid-methyl ester (Z) | 7.11 |
| 9 | 26.56 | Pentitol | 3.95 |
| 10 | 27.48 | Chrysine | 1.95 |
| 11 | 28.38 | Tricosane, Nonadecane | 1.12 |
| 12 | 29.01 | 1-Phenanthrenecarboxylic acid, 1,2,3,4a, 9,10a-octahydro1,4a-dimehyl1-7-(1-methylethy)-, methylester | 7.02 |
| 13 | 29.41 | Octadecane | 2.22 |
| 14 | 30.54 | Hexadecane | 1.80 |
| 15 | 30.86 | Phenol, 2,4-bis(1-methyl-1phenylethyl)-phenol | 13.88 |
| 16 | 31.07 | 2,4-Bis(dimethylbenzyl)-6-t-butyl phenol | 10.16 |
| 17 | 31.89 | 5,5-Dimethyl-6-(3-methyl-buta-1,3-dienyl)-7-oxa-bicyclo[4.1.0]hept-1-yl]-methanol | 4.68 |
| 18 | 33.59 | Octasiloxane | 5.06 |
| 19 | 33.87 | Octasiloxane | 3.01 |
| 20 | 35.12 | Octasiloxane | 3.46 |
| 21 | 35.14 | 1,14: 5,7-Dimethano-2H-[1,4]diazepino [2',3':3,4]cyclobuta[1,2-d][2,7] benzodiazecine | 2.16 |

Up to about 15% bio-crude oil could be harvested from the clam flesh along with other gaseous products. The energy value of the crude oil was 30-32 MJ/kg, close to that of petroleum based heavy oil (42 MJ/kg) and the viscosity of the crude oil. Higher carbon and hydrogen and lower oxygen

Example 9

Gas composition and other value added products: The gas analysis showed a gas composition of between about 55 to about 70% carbon dioxide, between about 1.70 to about 2.45% carbon monoxide, between about 1.90 to about 2.15% hydrogen, between about 3.02 to about 4.85% of methane and between about 4.71 to about 7.50% of methyl acetylene along with traces other hydrocarbon gases. Hydrogen, methane and methyl acetylene are high energy value gases and can be used as fuel gases after purification. The analysis of the aqueous phase from the reaction mixture showed ethanol as a major product (25 g/kg of algae) with formate and succinates as other co-products and had a pH of 8.80±0.39.

content of the bio-crude can make it an excellent source of fuel on further refining of the same.

Example 11

Use of poultry waste as algal nutrient: Questions to be answered: what are the total phosphate and total nitrogen removal rates for each algal strain?; and does corbicula effect algae production and if so are nutrient removal rates higher with corbicula treatment?

4 strains of Algae: *Chlorella sorokiniana* (Cso), *Chlamydomonos globosa* (Cg), *Scenedesmus bijuga* (Sb), *Chlorella minutissima* (Cm), and a consortium of Cm, Cg, and Sb. were used. Each strain was sampled for purity.

Medium: 12.5 g poultry waste/L; Raceway preparation: 5250 g waste/420 L in 5 separate bags; 6 hour extraction process; Algae was grow in BG11 growth media. It was harvested during the exponential growth phase, triple washed and resuspended in PL (90 ml). Poultry litter (PL) was inoculated with 10 ml algae, a 10% level. Biomass was measured using gravimetric filtration. Chlorophyll a analyzed using spectrophotometer. Total nitrogen and Total phosphorus levels were analyzed using HACH DR2700 spectrophotometer.

Figure 14:
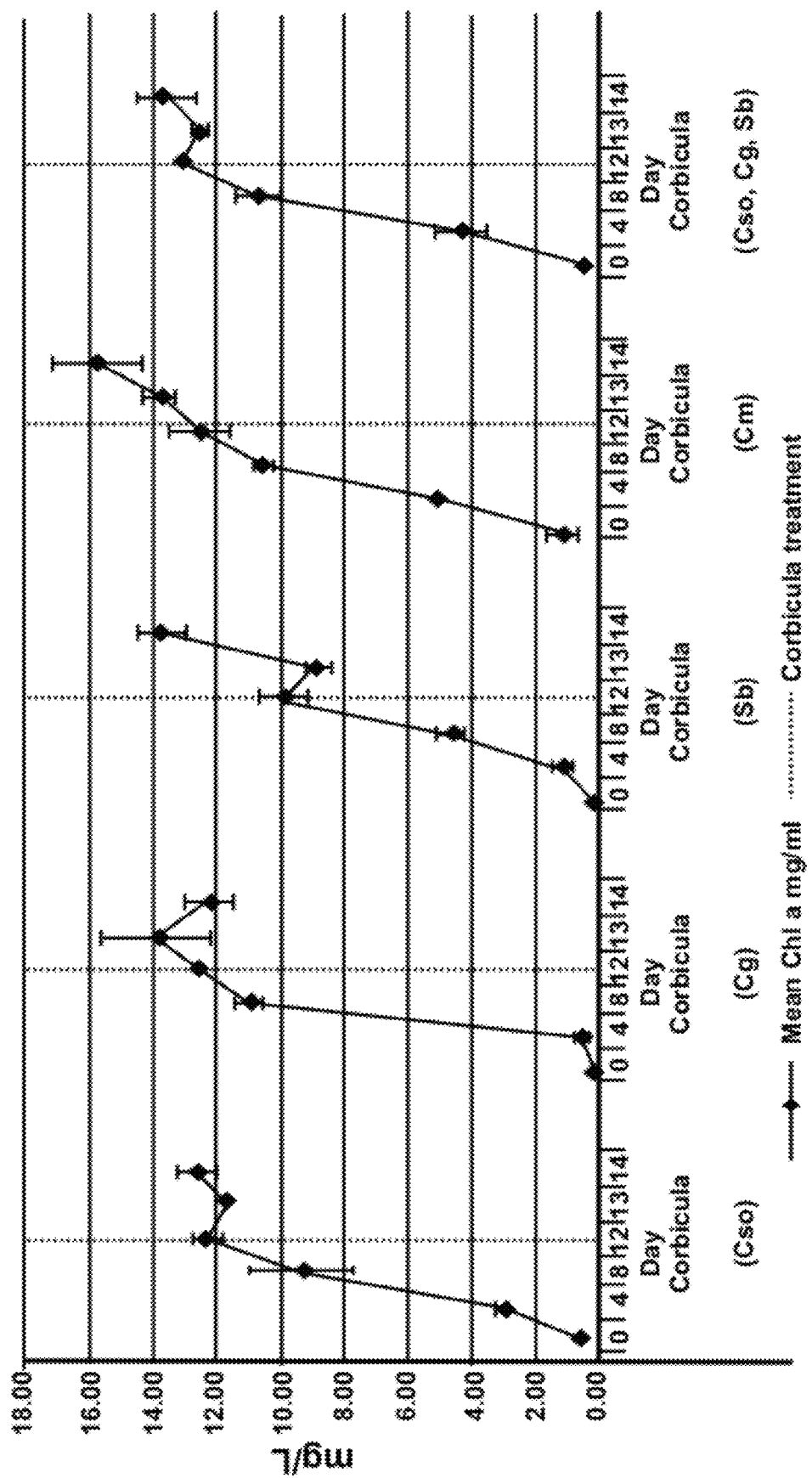
FIG. 14 is a series of graphs showing mean algal chlorophyll a concentrations before and after introduction of *corbicula* into poultry waste/algal mixtures.
Figure 15:
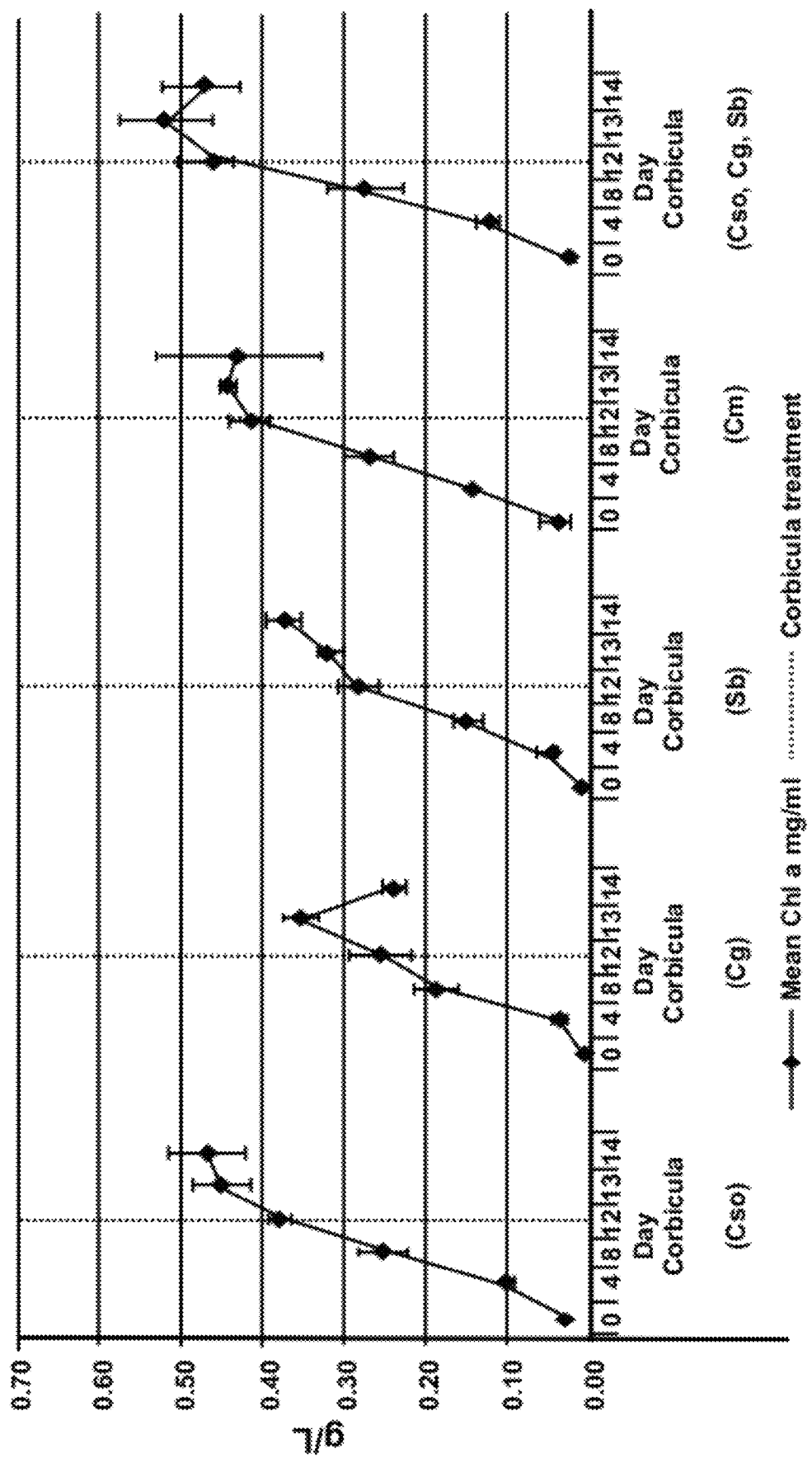
FIG. 15 is a series of graphs showing mean algal biomass concentration before and after introduction of *corbicula* into poultry waste/algal mixtures.

Pre-*corbicula* treatment: the consortium produced the highest levels of Chl a at 13 mg/L. Post *corbicula* treatment Cm produced the highest level of Chl a at 15.9 mg/L. Cso had the highest Total nitrogen removal from about 28 mg/L to about 60 mg/L=about 32 mg/U12 days approximately 2.7 mg/day, which continued through corbicula exposure. Cm also preformed well with relatively similar removal results. The consortium preformed well, although it contained high standard deviations. Cso and Sb showed the highest removal of phosphorus 9.5 mg/L-13.5 mg/L=about 0.33 mg/L/day. (See results in FIGS. 14 and 15).

Both samples showed increase removal during corbicula exposure at about 2.5 mg/L/day Sb, and 3 mg/L/day Cso. Algae was effective at nutrient removal.

Figure 16:
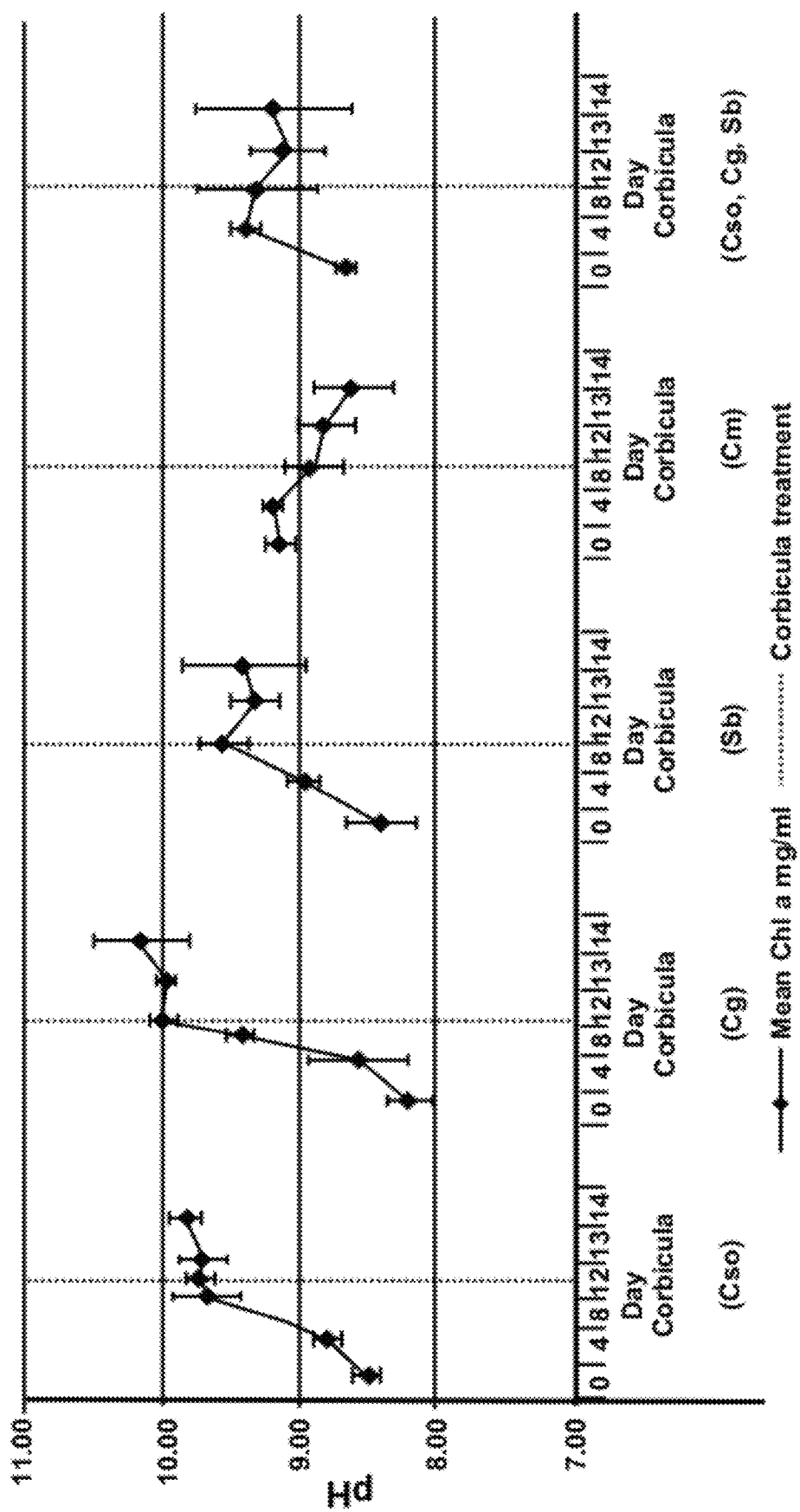
FIG. 16 is a series of graphs showing pH changes before and after introduction of corbicula into poultry waste/algal mixtures.
Figure 17:
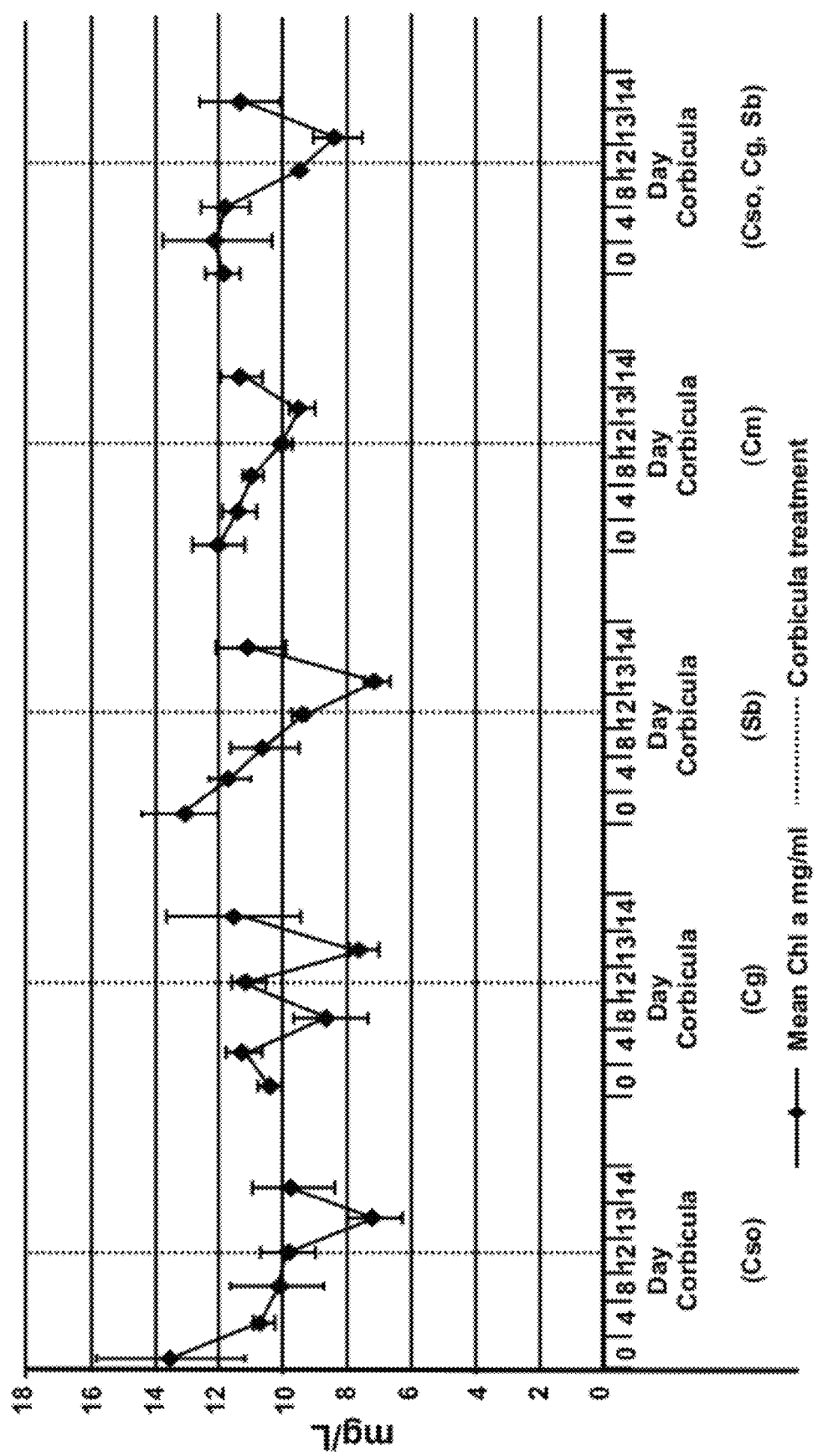
FIG. 17 is a series of graphs showing total phosphorus levels before and after introduction of *corbicula* into poultry waste/algal mixtures.
Figure 18:
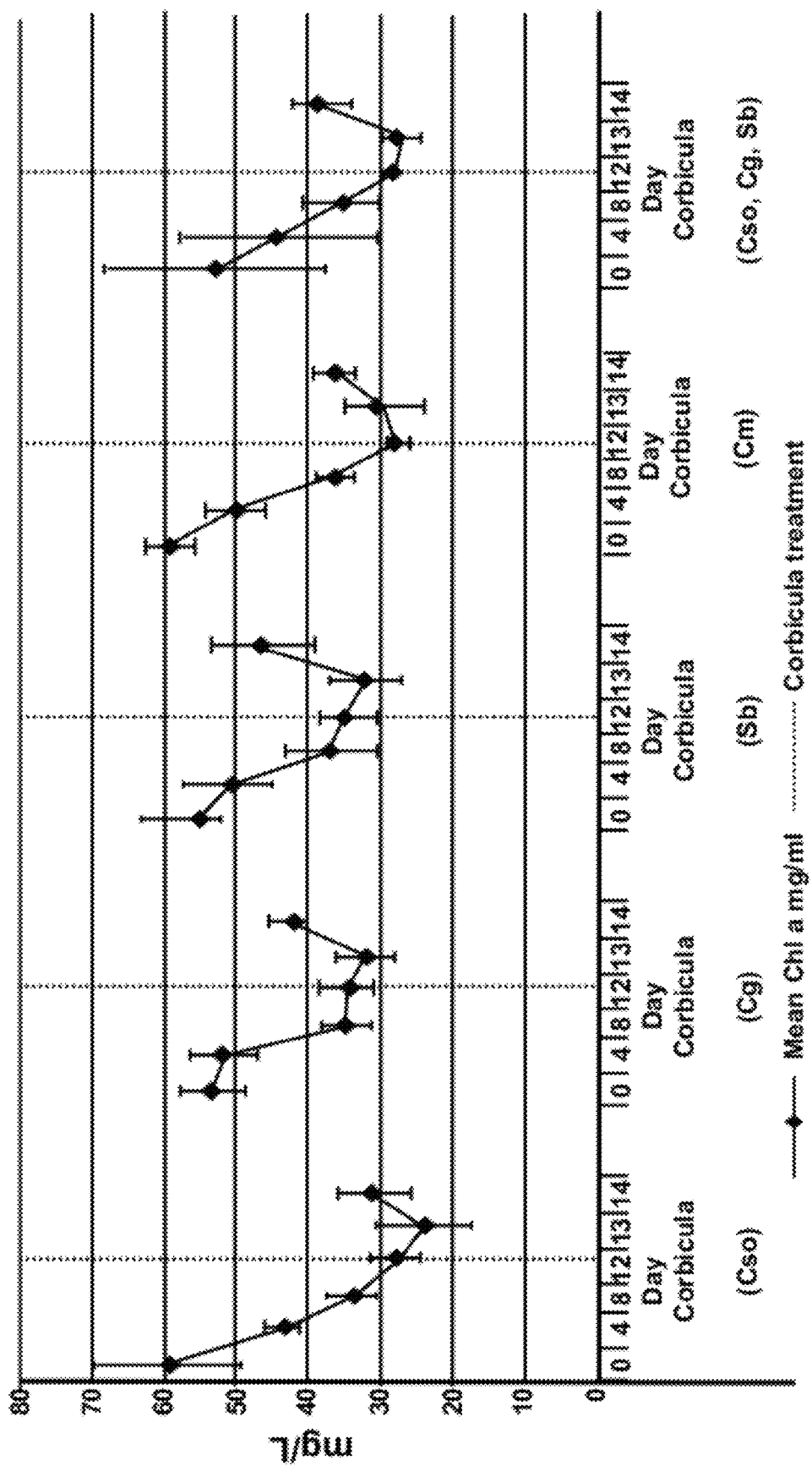
FIG. 18 is a series of graphs showing total nitrogen levels before and after introduction of corbicula into poultry waste/algal mixtures.

As shown in FIGS. 16-18, respectively, pH changes were recorded, as were Nitrogen removal rates for the best performing Algae that were sufficient to reduce the risk of environmental pollution (FIG. 17). Likewise, Phosphorus removal rates were both pre and post corbicula treatment were significant (FIG. 18).

Multiple factors may have played a role in the mortality of corbicula: the copper content of the poultry litter; high pH may also be toxic to corbicula.

We claim:

1. A method of generating a biofuel comprising:
   culturing a population of mollusks and a population of algal cells in a culture system suitable for maintaining the viability and proliferation of the mollusks the algal cells such that the population of the mollusks isolates a portion of the algal cells from the cultural system, and thereby generates an amount of a molluscan pseudofecal particulate material derived from the algal cells;
   isolating said pseudofecal particulate material from the culture system;
   isolating lipid matter from the pseudofecal particulate material; and
   generating a biofuel from the isolated lipid material.

2. The method of claim 1, wherein the population of mollusks is a population of freshwater mollusks, marine mollusks, or estuarine mollusks.

3. The method of claim 1, wherein the population of mollusks comprises at least one freshwater species selected from the group consisting of: a *Corbicula* sp., an *Anodonta* sp., a *Rangia* sp., a *Dreissena* sp., and a combination thereof.

4. The method of claim 1, wherein the population of mollusks comprises at least one marine species selected from the group consisting of: an *Ensis* sp., a *Tagelus* sp., a *Macoma* sp., a *Crassostrea* sp., a *Mya* sp., a *Rangia* sp., a *Polymesoda* sp., a *Perna* sp., and a combination thereof.

5. The method of claim 1, wherein the population of mollusks comprises at least one estuarine species selected from the group consisting of: a *Mytilus* sp., an *Anadara* sp., a *Noetia* sp., a *Mercenaria* sp., a *Pectiniae* sp., a *Geukensia* sp., an *Ischadium* sp., a *Petricola* sp., a *Cytropleura* sp., a *Tagelus* sp., and a combination thereof.

6. The method of claim 1, wherein the population of algal cells comprises at least one species selected from the group consisting of: a *Chlorella* sp., a *Chlamydomonas* sp., a *Scenedesmus* sp., an *Isochrysis* sp., a *Dunaliella* sp., a *Tetraselmis* sp., and a *Nannochloropsis* sp.

7. The method of claim 1, wherein the population of algal cells comprises at least one species selected from the group consisting of: *Scenedesmus bijuga, Chlorella minutissima, Chlorella sorokinia, Chlamydomonas globosa*, and a combination thereof.

8. The method of claim 1, wherein the population of algal cells comprises at least one species selected from the group consisting of: *Isochrysis galbana, Dunaliella tertiolecta, Tetraselmis suecica*, and *Nannochloropsis oculata*, and a combination thereof.

9. The method of claim 1, wherein the step of isolating the particulate matter from the culture system is selected from the group consisting of: a filtration method, a sedimentation method, a centrifugation method, a mechanical collection method, and a combination thereof.

10. The method of claim 1, wherein the step of isolating the lipid matter from the isolated pseudofecal particulate matter is selected from the group consisting of: a solvent extraction method, a steam extraction method, a chemical extraction method, a mechanical extraction method, an enzymatic extraction method, and a combination thereof.

11. The method of claim 1, further comprising the step of generating a biofuel from the tissues of the mollusks.

12. The method of claim 1, further comprising isolating lipid material from the tissues of the population of the bivalve mollusks.

13. The method of claim 12, wherein the step of isolating lipid material from the mollusk tissues includes a method selected from the group consisting of: a solvent extraction method, a steam extraction method, a chemical extraction method, a mechanical extraction method, or an enzymatic extraction method, and a combination thereof.

14. The method of claim 12, further comprising the step of generating a biofuel from the lipid material.

15. The method of claim 14 or 11, wherein the generation of a biofuel from the tissues of the mollusks is by a thermal conversion process.

\* \* \* \* \*